US010028657B2

(12) United States Patent
Friedman

(10) Patent No.: US 10,028,657 B2
(45) Date of Patent: Jul. 24, 2018

(54) SYSTEMS AND METHODS FOR MONITORING CROSS-LINKING ACTIVITY FOR CORNEAL TREATMENTS

(71) Applicant: Avedro, Inc., Waltham, MA (US)

(72) Inventor: Marc D. Friedman, Needham, MA (US)

(73) Assignee: Avedro, Inc., Waltham, MA (US)

( * ) Notice: Subject to any disclaimer, the term of this patent is extended or adjusted under 35 U.S.C. 154(b) by 0 days.

(21) Appl. No.: 15/161,302

(22) Filed: May 23, 2016

(65) Prior Publication Data
US 2016/0338588 A1 Nov. 24, 2016

Related U.S. Application Data

(60) Provisional application No. 62/165,741, filed on May 22, 2015.

(51) Int. Cl.
*G06K 9/00* (2006.01)
*A61B 3/14* (2006.01)
(Continued)

(52) U.S. Cl.
CPC .............. *A61B 3/145* (2013.01); *A61B 5/004* (2013.01); *A61B 5/0071* (2013.01);
(Continued)

(58) Field of Classification Search
None
See application file for complete search history.

(56) References Cited

U.S. PATENT DOCUMENTS

| | | |
|---|---|---|
| 3,169,459 A | 2/1965 | Friedberg et al. |
| 4,034,750 A | 7/1977 | Seiderman |

(Continued)

FOREIGN PATENT DOCUMENTS

| | | |
|---|---|---|
| DE | 102008046834 | 3/2010 |
| EP | 1285679 | 2/2003 |

(Continued)

OTHER PUBLICATIONS

Abahussin, M. "3D Collagen Orientation Study of the Human Cornea Using X-ray Diffraction and Femtosecond Laser Technology" Investigative Ophthalmology & Visual Science, Nov. 2009, vol. 50, No. 11, pp. 5159-5164.
Acosta A. et al., "Corneal Stroma Regeneration in Felines After Supradescemetic Keratoprothesis Implantation," Cornea, vol. 25, No. 7, pp. 830-838; Aug. 2006.
Averianova, O. S., "Nastoyaschee I buduschee kross-linkage." Mir Ofalmologii, 2010, [online] [retrieved on Feb. 13, 2014] Retrieved from the internet: http://miroft.org.ua/publications/.html.
Baier J. et al., "Singlet Oxygen Generation by UVA Light Exposure of Endogenous Photosensitizers," Biophysical Journal, vol. 91(4), pp. 1452-1459; Aug. 15, 2006.

(Continued)

*Primary Examiner* — Atiba O Fitzpatrick
(74) *Attorney, Agent, or Firm* — McDonnell Boehnen Hulbert & Berghoff LLP

(57) ABSTRACT

A system for treatment of corneal tissue includes one or more light sources that generate excitation light delivered to corneal tissue treated with a cross-linking agent. The excitation light causes the cross-linking agent to fluoresce by emitting an emission light at a plurality of emission wavelengths. The system includes an image capture system that captures image(s) of the corneal tissue. The image(s) indicate at least two of the emission wavelengths. The system includes a controller that receives the image(s). The controller: identifies each of the at least two emission wavelengths in the image(s); determines, from the image(s), respective characteristics associated separately with each of the at least two emission wavelengths; and provides information relating to cross-linking activity generated by the cross-linking agent in the corneal tissue based on the respective characteristics associated with each of the at least two emission wavelengths.

20 Claims, 11 Drawing Sheets

(51) Int. Cl.
    *A61K 31/525* (2006.01)
    *A61N 5/06* (2006.01)
    *A61B 5/00* (2006.01)
    *A61F 9/008* (2006.01)
    *A61F 9/007* (2006.01)

(52) U.S. Cl.
    CPC .......... *A61B 5/4836* (2013.01); *A61B 5/4848* (2013.01); *A61F 9/008* (2013.01); *A61F 9/0079* (2013.01); *A61K 31/525* (2013.01); *A61N 5/062* (2013.01); *A61F 2009/00872* (2013.01); *A61N 2005/0643* (2013.01); *A61N 2005/0661* (2013.01); *A61N 2005/0662* (2013.01)

(56) References Cited

U.S. PATENT DOCUMENTS

| | | |
|---|---|---|
| 4,161,013 A | 7/1979 | Grodzinsky et al. |
| 4,326,529 A | 4/1982 | Doss et al. |
| 4,381,007 A | 4/1983 | Doss |
| 4,665,913 A | 5/1987 | L'Esperance, Jr. |
| 4,712,543 A | 12/1987 | Baron |
| 4,764,007 A | 8/1988 | Task |
| 4,805,616 A | 2/1989 | Pao |
| 4,881,543 A | 11/1989 | Trembly et al. |
| 4,891,043 A | 1/1990 | Zeimer et al. |
| 4,969,912 A | 11/1990 | Kelman et al. |
| 4,994,058 A | 2/1991 | Raven et al. |
| 5,016,615 A | 5/1991 | Driller et al. |
| 5,019,074 A | 5/1991 | Muller |
| 5,098,426 A | 3/1992 | Sklar et al. |
| 5,103,005 A | 4/1992 | Gyure et al. |
| 5,171,254 A | 12/1992 | Sher |
| 5,171,318 A | 12/1992 | Gibson et al. |
| 5,281,211 A | 1/1994 | Parel et al. |
| 5,332,802 A | 7/1994 | Kelman et al. |
| 5,450,144 A | 9/1995 | Ben Nun |
| 5,461,212 A | 10/1995 | Seiler et al. |
| 5,490,849 A | 2/1996 | Smith |
| 5,512,966 A | 4/1996 | Snook |
| 5,562,656 A | 10/1996 | Sumiya |
| 5,608,472 A | 3/1997 | Szirth et al. |
| 5,618,284 A | 4/1997 | Sand |
| 5,624,437 A | 4/1997 | Freeman et al. |
| 5,634,921 A | 6/1997 | Hood et al. |
| 5,766,171 A | 6/1998 | Silvestrini |
| 5,779,696 A | 7/1998 | Berry et al. |
| 5,786,893 A | 7/1998 | Fink et al. |
| 5,814,040 A | 9/1998 | Nelson et al. |
| 5,885,275 A | 3/1999 | Muller |
| 5,891,131 A | 4/1999 | Rajan et al. |
| 5,910,110 A | 6/1999 | Bastable |
| 6,033,396 A | 3/2000 | Huang et al. |
| 6,099,521 A | 8/2000 | Shadduck |
| 6,101,411 A | 8/2000 | Newsome |
| 6,104,959 A | 8/2000 | Spertell |
| 6,139,876 A | 10/2000 | Kolta |
| 6,161,544 A | 12/2000 | DeVore et al. |
| 6,162,210 A | 12/2000 | Shadduck |
| 6,188,500 B1 | 2/2001 | Rudeen et al. |
| 6,218,360 B1 | 4/2001 | Cintron et al. |
| 6,223,075 B1 | 4/2001 | Beck et al. |
| 6,270,221 B1 | 8/2001 | Liang et al. |
| 6,280,436 B1 | 8/2001 | Freeman et al. |
| 6,293,938 B1 | 9/2001 | Muller et al. |
| 6,319,273 B1 | 11/2001 | Chen et al. |
| 6,322,557 B1 | 11/2001 | Nikolaevich et al. |
| 6,325,792 B1 | 12/2001 | Swinger et al. |
| 6,334,074 B1 | 12/2001 | Spertell |
| 6,342,053 B1 | 1/2002 | Berry |
| 6,394,999 B1 | 5/2002 | Williams et al. |
| 6,402,739 B1 | 6/2002 | Neev |
| 6,413,255 B1 | 7/2002 | Stern |
| 6,478,792 B1 | 11/2002 | Hansel |
| 6,520,956 B1 | 2/2003 | Huang |
| 6,520,958 B1 | 2/2003 | Shimmick et al. |
| 6,537,545 B1 | 3/2003 | Karageozian et al. |
| 6,571,118 B1 | 5/2003 | Utzinger et al. |
| 6,572,849 B2 | 6/2003 | Chicaning, Jr. |
| 6,617,963 B1 | 9/2003 | Watters et al. |
| 6,673,067 B1 | 1/2004 | Peyman |
| 6,918,904 B1 | 7/2005 | Peyman |
| 6,946,440 B1 | 9/2005 | DeWoolfson et al. |
| 7,001,374 B2 | 2/2006 | Peyman |
| 7,004,902 B2 | 2/2006 | Luce |
| 7,044,945 B2 | 5/2006 | Sand |
| 7,073,510 B2 | 7/2006 | Redmond et al. |
| 7,130,835 B2 | 10/2006 | Cox et al. |
| 7,141,049 B2 | 11/2006 | Stern et al. |
| 7,192,429 B2 | 3/2007 | Trembly |
| 7,237,898 B1 | 7/2007 | Hohla et al. |
| 7,270,658 B2 | 9/2007 | Woloszko et al. |
| 7,302,189 B2 | 11/2007 | Kawahata |
| 7,331,350 B2 | 2/2008 | Kochevar et al. |
| 7,402,562 B2 | 7/2008 | DeWoolfson et al. |
| 7,753,943 B2 | 7/2010 | Strong |
| 7,871,378 B1 | 1/2011 | Chou et al. |
| 7,898,656 B2 | 3/2011 | Yun et al. |
| 7,935,058 B2 | 5/2011 | Dupps, Jr. et al. |
| 8,111,394 B1 | 2/2012 | Borysow et al. |
| 8,115,919 B2 | 2/2012 | Yun et al. |
| 8,366,689 B2 | 2/2013 | Marshall et al. |
| 8,414,911 B2 | 4/2013 | Mattson et al. |
| 8,475,437 B2 | 7/2013 | Mrochen et al. |
| 8,574,277 B2 | 11/2013 | Muller et al. |
| 8,715,273 B2 | 5/2014 | Thyzel |
| 8,995,618 B2 | 3/2015 | Gertner |
| 9,005,261 B2 | 4/2015 | Brinkmann |
| 2001/0041856 A1 | 11/2001 | McDaniel |
| 2001/0047012 A1 | 11/2001 | Desantis, Jr. |
| 2001/0055095 A1 | 12/2001 | D'Souza et al. |
| 2002/0002369 A1 | 1/2002 | Hood |
| 2002/0013577 A1 | 1/2002 | Frey et al. |
| 2002/0042638 A1 | 4/2002 | Iezzi et al. |
| 2002/0049437 A1 | 4/2002 | Silvestrini |
| 2002/0099363 A1 | 7/2002 | Woodward et al. |
| 2002/0159618 A1 | 10/2002 | Freeman et al. |
| 2002/0164379 A1 | 11/2002 | Nishihara et al. |
| 2003/0018255 A1 | 1/2003 | Martin et al. |
| 2003/0030908 A1 | 2/2003 | Cheng et al. |
| 2003/0135122 A1 | 7/2003 | Bambot et al. |
| 2003/0175259 A1 | 9/2003 | Karageozian et al. |
| 2003/0189689 A1 | 10/2003 | Rathjen |
| 2003/0208190 A1 | 11/2003 | Roberts et al. |
| 2003/0216728 A1 | 11/2003 | Stern et al. |
| 2003/0231285 A1 | 12/2003 | Ferguson |
| 2004/0001821 A1 | 1/2004 | Silver et al. |
| 2004/0002694 A1 | 1/2004 | Pawlowski et al. |
| 2004/0071778 A1 | 4/2004 | Bellmann et al. |
| 2004/0093046 A1 | 5/2004 | Sand |
| 2004/0111086 A1 | 6/2004 | Trembly |
| 2004/0143250 A1 | 7/2004 | Trembly |
| 2004/0199079 A1 | 10/2004 | Chuck et al. |
| 2004/0199158 A1 | 10/2004 | Hood et al. |
| 2004/0204707 A1 | 10/2004 | Hood et al. |
| 2004/0243160 A1 | 12/2004 | Shiuey et al. |
| 2004/0254520 A1 | 12/2004 | Porteous et al. |
| 2005/0038471 A1 | 2/2005 | Chan et al. |
| 2005/0096515 A1 | 5/2005 | Geng |
| 2005/0149006 A1 | 7/2005 | Peyman |
| 2005/0187599 A1 | 8/2005 | Sharkey et al. |
| 2005/0271590 A1 | 12/2005 | Schwartz et al. |
| 2006/0058592 A1 | 3/2006 | Bouma et al. |
| 2006/0106371 A1 | 5/2006 | Muhlhoff et al. |
| 2006/0135957 A1 | 6/2006 | Panescu |
| 2006/0149343 A1 | 7/2006 | Altshuler et al. |
| 2006/0177430 A1 | 8/2006 | Bhushan et al. |
| 2006/0189964 A1 | 8/2006 | Anderson et al. |
| 2006/0195074 A1 | 8/2006 | Bartoli |
| 2006/0195076 A1 | 8/2006 | Blumenkranz et al. |
| 2006/0276777 A1 | 12/2006 | Coroneo |
| 2006/0287662 A1 | 12/2006 | Berry et al. |
| 2007/0024860 A1 | 2/2007 | Tobiason et al. |

(56) References Cited

U.S. PATENT DOCUMENTS

| | | |
|---|---|---|
| 2007/0027509 A1 | 2/2007 | Eisenberg et al. |
| 2007/0028928 A1 | 2/2007 | Peyman |
| 2007/0048340 A1 | 3/2007 | Ferren et al. |
| 2007/0055227 A1 | 3/2007 | Khalaj et al. |
| 2007/0074722 A1 | 4/2007 | Giroux et al. |
| 2007/0090153 A1 | 4/2007 | Naito et al. |
| 2007/0099966 A1 | 5/2007 | Fabricant |
| 2007/0123845 A1 | 5/2007 | Lubatschowski |
| 2007/0135805 A1 | 6/2007 | Peyman |
| 2007/0142828 A1 | 6/2007 | Peyman |
| 2007/0161976 A1 | 7/2007 | Trembly |
| 2007/0203478 A1 | 8/2007 | Herekar |
| 2007/0203547 A1 | 8/2007 | Costello et al. |
| 2007/0244470 A1 | 10/2007 | Barker, Jr. et al. |
| 2007/0244496 A1 | 10/2007 | Hellenkamp |
| 2007/0265603 A1 | 11/2007 | Pinelli |
| 2008/0009901 A1 | 1/2008 | Redmond et al. |
| 2008/0015660 A1 | 1/2008 | Herekar |
| 2008/0027328 A1 | 1/2008 | Klopotek et al. |
| 2008/0033408 A1 | 2/2008 | Bueler et al. |
| 2008/0063627 A1 | 3/2008 | Stucke et al. |
| 2008/0114283 A1 | 5/2008 | Mattson et al. |
| 2008/0139671 A1 | 6/2008 | Herekar |
| 2008/0208177 A1 | 8/2008 | Mrochen et al. |
| 2009/0024117 A1 | 1/2009 | Muller |
| 2009/0054879 A1 | 2/2009 | Berry |
| 2009/0069798 A1 | 3/2009 | Muller et al. |
| 2009/0116096 A1 | 5/2009 | Lalevsky et al. |
| 2009/0130176 A1 | 5/2009 | Bossy-Nobs et al. |
| 2009/0149842 A1 | 6/2009 | Muller et al. |
| 2009/0149923 A1 | 6/2009 | Herekar |
| 2009/0171305 A1 | 7/2009 | El Hage |
| 2009/0192437 A1 | 7/2009 | Soltz et al. |
| 2009/0209954 A1 | 8/2009 | Muller et al. |
| 2009/0234335 A1 | 9/2009 | Yee |
| 2009/0271155 A1 | 10/2009 | Dupps, Jr. et al. |
| 2009/0275929 A1 | 11/2009 | Zickler |
| 2009/0276042 A1 | 11/2009 | Hughes et al. |
| 2010/0028407 A1 | 2/2010 | Del Priore et al. |
| 2010/0036488 A1 | 2/2010 | de Juan, Jr. et al. |
| 2010/0057060 A1 | 3/2010 | Herekar |
| 2010/0069894 A1 | 3/2010 | Mrochen et al. |
| 2010/0082018 A1 | 4/2010 | Panthakey et al. |
| 2010/0094197 A1 | 4/2010 | Marshall et al. |
| 2010/0114109 A1 | 5/2010 | Peyman |
| 2010/0149487 A1 | 6/2010 | Ribak |
| 2010/0173019 A1 | 7/2010 | Paik et al. |
| 2010/0189817 A1 | 7/2010 | Krueger et al. |
| 2010/0191228 A1 | 7/2010 | Ruiz et al. |
| 2010/0203103 A1 | 8/2010 | Dana et al. |
| 2010/0204584 A1 | 8/2010 | Omberg et al. |
| 2010/0210996 A1 | 8/2010 | Peyman |
| 2010/0271593 A1 | 10/2010 | Filar |
| 2010/0286156 A1 | 11/2010 | Pinelli |
| 2010/0317588 A1 | 12/2010 | Shoseyov et al. |
| 2010/0318017 A1 | 12/2010 | Lewis et al. |
| 2011/0044902 A1 | 2/2011 | Weiner et al. |
| 2011/0077624 A1 | 3/2011 | Brady et al. |
| 2011/0098790 A1 | 4/2011 | Daxer |
| 2011/0118654 A1 | 5/2011 | Muller et al. |
| 2011/0125076 A1 | 5/2011 | Kraft et al. |
| 2011/0152219 A1 | 6/2011 | Stagni |
| 2011/0190742 A1 | 8/2011 | Anisimov |
| 2011/0202114 A1 | 8/2011 | Kessel et al. |
| 2011/0208300 A1 | 8/2011 | de Juan, Jr. et al. |
| 2011/0237999 A1 | 9/2011 | Muller et al. |
| 2011/0264082 A1 | 10/2011 | Mrochen et al. |
| 2011/0288466 A1 | 11/2011 | Muller et al. |
| 2011/0301524 A1 | 12/2011 | Bueler et al. |
| 2012/0083772 A1 | 4/2012 | Rubinfeld et al. |
| 2012/0140238 A1 | 6/2012 | Horn et al. |
| 2012/0203051 A1 | 8/2012 | Brooks et al. |
| 2012/0203161 A1 | 8/2012 | Herekar |
| 2012/0209051 A1 | 8/2012 | Blumenkranz et al. |
| 2012/0215155 A1 | 8/2012 | Muller et al. |
| 2012/0283621 A1 | 11/2012 | Muller |
| 2012/0289886 A1 | 11/2012 | Muller et al. |
| 2012/0302862 A1 | 11/2012 | Yun et al. |
| 2012/0303008 A1 | 11/2012 | Muller et al. |
| 2012/0310083 A1 | 12/2012 | Friedman et al. |
| 2012/0310223 A1 | 12/2012 | Knox et al. |
| 2013/0060187 A1 | 3/2013 | Friedman et al. |
| 2013/0085370 A1 | 4/2013 | Friedman et al. |
| 2013/0116757 A1 | 5/2013 | Russmann |
| 2013/0245536 A1 | 9/2013 | Friedman et al. |
| 2013/0310732 A1 | 11/2013 | Foschini et al. |
| 2014/0066835 A1 | 3/2014 | Muller et al. |
| 2014/0194957 A1 | 7/2014 | Rubinfeld et al. |
| 2014/0249509 A1 | 9/2014 | Rubinfeld et al. |
| 2014/0276361 A1 | 9/2014 | Herekar et al. |
| 2014/0277431 A1 | 9/2014 | Herekar et al. |
| 2014/0343480 A1 | 11/2014 | Kamaev et al. |
| 2014/0368793 A1 | 12/2014 | Friedman et al. |
| 2015/0085252 A1 | 3/2015 | Fujimura et al. |
| 2016/0139390 A1 | 5/2016 | Bukshtab et al. |
| 2016/0175442 A1 | 6/2016 | Kamaev et al. |

FOREIGN PATENT DOCUMENTS

| | | |
|---|---|---|
| EP | 1561440 | 8/2005 |
| EP | 1790383 | 5/2007 |
| EP | 2253321 | 11/2010 |
| IT | MI2010A001236 | 5/2010 |
| JP | 2000/262476 | 9/2000 |
| KG | 1376 | 8/2011 |
| RU | 2086215 | 8/1997 |
| RU | 2098057 | 12/1997 |
| RU | 2121825 | 11/1998 |
| RU | 2127099 | 3/1999 |
| RU | 2127100 | 3/1999 |
| RU | 2309713 | 11/2007 |
| RU | 2359716 | 6/2009 |
| RU | 2420330 | 6/2011 |
| RU | 2428152 | 9/2011 |
| RU | 2456971 | 7/2012 |
| WO | 93/16631 | 9/1993 |
| WO | 94/03134 | 2/1994 |
| WO | 00/74648 | 12/2000 |
| WO | 01/58495 | 8/2001 |
| WO | 03/061696 | 7/2003 |
| WO | 2004/052223 | 6/2004 |
| WO | 2005/110397 | 11/2005 |
| WO | 2006/012947 | 2/2006 |
| WO | 2006/128038 | 11/2006 |
| WO | 2007/001926 | 1/2007 |
| WO | 2007/053826 | 5/2007 |
| WO | 2007/081750 | 7/2007 |
| WO | 2007/120457 | 10/2007 |
| WO | 2007/128581 | 11/2007 |
| WO | 2007/139927 | 12/2007 |
| WO | 2007/143111 | 12/2007 |
| WO | 2008/000478 | 1/2008 |
| WO | 2008/052081 | 5/2008 |
| WO | 2008/095075 | 8/2008 |
| WO | 2009/042159 | 4/2009 |
| WO | 2009/073213 | 6/2009 |
| WO | 2009/114513 | 9/2009 |
| WO | 2009/146151 | 12/2009 |
| WO | 2010/011119 | 1/2010 |
| WO | 2010/015255 | 2/2010 |
| WO | 2010/023705 | 3/2010 |
| WO | 2010/039854 | 4/2010 |
| WO | 2010/093908 | 8/2010 |
| WO | 2011/019940 | 2/2011 |
| WO | 2011/050360 | 4/2011 |
| WO | 2011/116306 | 9/2011 |
| WO | 2012/004726 | 1/2012 |
| WO | 2012/047307 | 4/2012 |
| WO | 2012/149570 | 11/2012 |
| WO | 2012/158991 | 11/2012 |
| WO | 2012/174453 | 12/2012 |
| WO | 2013/062910 | 5/2013 |
| WO | 2013/148713 | 10/2013 |
| WO | 2013/148895 | 10/2013 |

(56) References Cited

FOREIGN PATENT DOCUMENTS

| WO | 2013/149075 | 10/2013 |
|---|---|---|
| WO | 2014/081875 | 5/2014 |
| WO | 2014/145666 | 9/2014 |
| WO | 2014/202736 | 12/2014 |
| WO | 2016069628 | 5/2016 |

OTHER PUBLICATIONS

Ballou, D. et al., "Direct Demonstration of Superoxide Anion Production During the Oxidation of Reduced Flavin and of Its Catalytic Decomposition by Erythrocuprein," Biochemical and Biophysical Research Communications vol. 36, No. 6, pp. 898-904, Jul. 11, 1969.

Barbarino, S. et al., "Post-LASIK ectasia: Stabilization and Effective Management with Riboflavin / ultraviolet A-induced collagen cross-linking," Association for Research in Vision and Ophthalmology, 2006.

Berjano E., et al., "Radio-Frequency Heating of the Cornea: Theoretical Model and In Vitro Experiments," IEEE Transactions on Biomedical Engineering, vol. 49, No. 3, pp. 196-205; Mar. 2002.

Berjano E., et al., "Ring Electrode for Radio-frequency Heating of the Cornea: Modelling and in vitro Experiments," Medical & Biological Engineering & Computing, vol. 41, pp. 630-639; Jun. 2003.

Brüel, A., "Changes in Biomechanical Properties, Composition of Collagen and Elastin, and Advanced Glycation Endproducts of the Rat Aorta in Relation to Age," Atherosclerosis 127, Mar. 14, 1996.

Burke, JM et al., Abstract for "Retinal proliferation in response to vitreous hemoglobin or iron", Investigative Ophthalmology & Visual Science, May 1981, 20(5), pp. 582-592.

Chai, D. et al., "Quantitative Assessment of UVA-Riboflavin Corneal Cross-Linking Using Nonlinear Optical Microscopy," Investigative Ophthalmology & Visual Science, Jun. 2011, vol. 52, No. 7, 4231-4238.

Chan B.P., et al., "Effects of photochemical crosslinking on the microstructure of collagen and a feasibility study on controlled protein release;" Acta Biomaterialia, vol. 4, Issue 6, pp. 1627-1636; Jul. 1, 2008.

Chandonnet, "CO2 Laser Annular Thermokeratoplasty: A Preliminary Study," Lasers in Surgery and Medicine, vol. 12, pp. 264-273; 1992.

Chace, KV. et al., Abstract for "The role of nonenzymatic glycosylation, transition metals, and free radicals in the formation of collagen aggregates", Arch Biochem Biophys., Aug. 1, 1991, 288(2), pp. 473-480.

Clinical Trials.gov, "Riboflavin Mediated Corneal Crosslinking for Stabilizing Progression of Keratoconus (CCL)," University Hospital Freiburg, Feb. 20, 2008; retrieved from http://www.clinicaltrials.gov/ct2/show/NCT00626717, on Apr. 26, 2011.

Corbett M., et al., "Effect of Collagenase Inhibitors on Corneal Haze after PRK," Exp. Eye Res., vol. 72, Issue 3, pp. 253-259; Jan. 2001.

Coskenseven E. et al., "Comparative Study of Corneal Collagen Cross-linking With Riboflavin and UVA Irradiation in Patients With Keratoconus," Journal of Refractive Surgery, vol. 25, issue 4, pp. 371-376; Apr. 2009.

"Definity (perflutren) injection, suspension [Bristol-Myers Squibb Medical Imaging]," http://dailymed.nlm.nih.gov/dailymed/drugInfo.cfm?id=8338, revised Sep. 2008, retrieved via the internet archive from http://web.archive.org/web/20100321105500/http://dailymed.nlm.nih.gov/dailymed/drugInfo.cfm?id=8338, on Dec. 14, 2011.

Ehlers W., et al., "Factors Affecting Therapeutic Concentration of Topical Aminocaproic Acid in Traumatic Hyphema," Investigative Ophthalmology & Visual Science, vol. 31, No. 11, pp. 2389-2394; Nov. 1990.

Erskine H., "Avedro Becomes Sponsor of US FDA Clinical Trials of Corneal Collagen Crosslinking," Press Release, Mar. 16, 2010 (1 page).

Fite et al., "Noninvasive Multimodal Evaluation of Bioengineered Cartilage Constructs Combining Time-Resolved Fluorescence and Ultrasound Imaging." Tissue Eng: Part C vol. 17, No. 4, 2011.

Friedman, M. et al. "Advanced Corneal Cross-Linking System with Fluorescence Dosimetry", Journal of Ophthalmology, vol. 2012, Article ID 303459, dated May 7, 2012.

Frucht-Pery, et al. "Iontophoresis—gentamicin delivery into the rabbit cornea, using a hydrogel delivery probe," Jun. 20, 2003.

Gibson, Q. et al., "The Oxidation of Reduced Flavin Mononucleotide by Molecular Oxygen," Biochem. J. (1962) 83, 368-377.

Givens et al. "A Photoactivated Diazpryruvoyl Cross-Linking Agent for Bonding Tissue Containing Type-I Collagen." Photochemistry and Photobiology. vol. 78, No. 1, 2003 (pp. 23-29).

Glenn J.V., et al., "Advanced Glycation End Product (AGE) Accumulation on Bruch's Membrane: Links to Age-Related RPE Dysfunction;" Investigative Ophthalmology & Visual Science, vol. 50, No. 1, pp. 441-451; Jan. 2009.

Gravitz L., "Laser Show in the Surgical Suite: Lasers and a century-old dye could supplant needles and thread;" technology review, MIT, Mar./Apr. 2009; retrieved from http://www.technologyreview.com/biomedicine/22088/?nlid=1767, on Sep. 26, 2011.

Hafezi F., et al., "Collagen Crosslinking with Ultraviolet-A and Hypoosmolar Riboflavin Solution in Thin Corneas," J. Catract Refract. Surg., vol. 35, No. 1, pp. 621-624; Apr. 2009.

Hammer Arthur et al., "Corneal Biomechanical Properties at different Corneal Cross-Linking (CXL) Irradiances," IOVS, May 2014, vol. 55, No. 5, pp. 2881-2884.

Hitzenberger et al., "Birefringence Properties of the Human Cornea Measured With Polarization Sensitive Optical Coherence Tomography," Bull. Soc. Beige Ophtalmol., 302, 153-168, 2006.

Holmström, B. et al., "Riboflavin as an Electron Donor in Photochemical Reactions," 1867-1871, Nov. 29, 1960.

How to Use Definity: "Frequently Asked Questions;" retrieved from http://www.definityimaging.com/how-faq.html, on Sep. 26, 2011 (3 pages) (date unknown, prior to Apr. 26, 2010).

IMEX, "KXL System: Crosslinking Para Cirugia Corneal Bibliografia Cientifica," Product Literature, Nov. 23, 2010.

Kamaev et al., "Photochemical Kinetics of Corneal Cross-Linking With Riboflavin," Investigative Ophthalmology & Visual Science, Apr. 2012, vol. 53, No. 4, pp. 2360-2367 (8 pages).

Kampik D. et al., "Influence of Corneal Collagen Crosslinking With Riboflavin and Ultraviolet-A Irradiation on Excimer Laser Surgery," Investigative Ophthalmology & Visual Science, vol. 51, No. 8, pp. 3929-3934; Aug. 2010.

Kanellopoulos, A. J., "Collagen Cross-linking in Early Keratoconus With Riboflavin in a Femtosecond Laser-created Pocket: Initial Clinical Results", Journal of Refractive Surgery, Aug. 18, 2009.

Kanellopoulos, A. J., "Keratoconus management: UVA-induced collagen cross-linking followed by a limited topo-guided surface excimer ablation," American Academy of Ophthalmology, 2006 (25 pages).

Kanellopoulos, A. J., "Ultraviolet A cornea collagen cross-linking, as a pre-treatment for surface excimer ablation in the management of keratoconus and post-LASIK ectasia," American Academy of Ophthalmology, 2005 (28 pages).

Kissner Anja, et al., "Pharmacological Modification of the Epithelial Permeability by Benzalkonium Chloride in UVA/Riboflavin Corneal Collagen Cross-Linking," Current Eye Research 35(8), pp. 715-721; Mar. 2010 (7 pages).

Koller, T. et. Al., "Complication and failure rates after corneal crosslinking," Journal Cataract and refractive surgery, vol. 35, No. 8, Aug. 2009, pp. 1358-1362.

Koller T., et al., "Therapeutische Quervernetzung der Hornhaut mittels UVA and Riboflavin: Therapeutic Cross-Linking of the Cornea Using Riboflavin/UVA," Klinische Monatsblätter für Augenheilkunde, vol. 224, No. 9, pp. 700-706; Sep. 2007 (7 pages).

Krueger, Ronald R., "Rapid VS Standard Collagen CXL with Equivalent Energy Dosing," presentation slides; available at http://www.slideshare.net/logen/krueger-herekar-rapid-cross-linking (date unknown, prior to Nov. 9, 2009) (26 pages).

(56) References Cited

OTHER PUBLICATIONS

Massey, V., "Activation of Molecular Oxygen by Flavins and Flavoproteins," The Journal of Biological Chemistry vol. 269, No. 36, Issue of Sep. 9, pp. 22459-22462, 1994 (4 pages).
Marzouky, et. al., Tensioactive-mediated Transepithelial Corneal Cross-linking—First Laboratory Report, European Ophthalmic Review, 2009, 3(2), pp. 67-70.
Lee et al., "Spectrally filtered Raman / Thomson scattering using a rubidium Vapor filter ", AIAA J. 40, pp. 2504-2510 (2002).
Li, C. et al."Elastic Properties of Soft Tissue-Mimicking Phantoms Assessed by Combined Use of Laser Ultrasonics and Low Coherence Interferometry." Optics Express. vol. 19, No. 11, May 9, 2011 (pp. 10153-10163).
Li, C. et al. "Noncontact All-Optical Measurement of Corneal Elasticity." Optics Letters. vol. 37, No. 10, May 15, 2012 (pp. 1625-1627).
Li, P. et al. "In Vivo Microstructural and Microvascular Imaging of the Human Corneo-Scleral Limbus Using Optical Coherence Tomography." Biomedical Optics Express. vol. 2, No. 11, Oct. 18, 2011 (pp. 3109-3118).
Meek, K.M. et al. "The Cornea and Scleera", Collagen: Structure and Mechanics, Chapter 13, pp. 359-396, 2008 (38 pages).
Mi S., et al., "The adhesion of LASIK-like flaps in the cornea: effects of cross-linking, stromal fibroblasts and cytokine treatment," presented at British Society for Matrix Biology annual Meeting, Cardiff, UK, Sep. 8-9, 2008 (17 pages).
Muller L., et al., "The Specific Architecture of the Anterior Stroma Accounts for Maintenance of Corneal Curvature," Br. J. Opthalmol., vol. 85, pp. 437-443; Apr. 2001 (8 pages).
Mulroy L., et al., "Photochemical Keratodesmos for repair of Lamellar corneal Incisions;" Investigative Ophthalmology & Visual Science, vol. 41, No. 11, pp. 3335-3340; Oct. 2000 (6 pages).
Naoumidi T., et al., "Two-Year Follow-up of Conductive Keratoplasty for the Treatment of Hyperopic Astigmatism," J. Cataract Refract. Surg., vol. 32(5), pp. 732-741; May 2006 (10 pages).
Nesterov, A. P. "Transpalpebralny Tonometr Dlya lzmereniya Vnutriglaznogo Davleniya." Feb. 2, 2006. [online] [Retrieved Dec. 17, 2012] Retrieved from the Internet: <URL: http://grpz.ru/images/publication_pdf/27.pdf>.
O'Neil A.C., et al., "Microvascular Anastomosis Using a Photochemical Tissue Bonding Technique;" Lasers in Surgery and Medicine, vol. 39, Issue 9, pp. 716-722; Oct. 2007 (7 pages).
O.V. Shilenskaya et al., "Vtorichnaya katarakta posle implantatsii myagkikh IOL," [online] Aug. 8, 2008 [retrieved Mar. 4, 2013] Retrieved from the Internet: <URL:http://www.reper.ru/rus/index.php?catid=210> (4 pages).
Paddock C., Medical News Today: "Metastatic Melanoma PV-10 Trial Results Encouraging Says Drug Company;" Jun. 9, 2009; retrieved from http://www.medicalnewstoday.com/articles/153024.php, on Sep. 26, 2011 (2 pages).
Pallikaris I., et al., "Long-term Results of Conductive Keratoplasty for low to Moderate Hyperopia," J. Cataract Refract. Surg., vol. 31(8), pp. 1520-1529; Aug. 2005 (10 pages).
Pinelli, R. "Corneal Cross-Linking with Riboflavin: Entering a New Era in Ophthalmology." Ophthalmology Times Europe. vol. 2, No. 7, Sep. 1, 2006, [online], [retrieved on May 20, 2013]. Retrieved from the Internet: <URL: http://www.oteurope.com/ophthalmologytimeseurope/Cornea/Corneal-cross-linking-with-riboflavin-entering-a-n/ArticleStandard/Article/detail/368411> (3 pages).
Pinelli R., et al., "C3-Riboflavin Treatments: Where Did We Come From? Where Are We Now?" Cataract & Refractive Surgery Today Europe, Summer 2007, pp. 36-46; Jun. 2007 (10 pages).
Pinelli, R., "Panel Discussion: Epithelium On/Off, Corneal abrasion for CCL contra", presented at the 3° International Congress of Corneal Cross Linking on Dec. 7-8, 2007 in Zurich (36 pages).
Roberto Pinelli et al, "Transepithelial Tensioactive Mediated CXL", Cataract & Refractive Surgery Today Europe, p. 1, URL: http://bmctoday.net/crstodayeurope/pdfs/0409_09.pdf, XP055158069.
Pinelli R., "Resultados de la Sociedad de Cirugia Refractiva Italiana (SICR) utilizando el C3-R" presented at the Istitutor Laser Microchirurgia Oculare in 2007 in Italy (23 pages).
Pinelli et al., "Tensioactive-mediated Transepithelial Corneal Cross-linking—First Laboratory Report", 2009, European Ophthalmic Review, 3(2), pp. 67-70.
Pinelli R., "The Italian Refractive Surgery Society (SICR) results using C3-R" presented Jun. 22-23, 2007 in Italy (13 pages).
Ponce C., et al., "Central and Peripheral Corneal Thickness Measured with Optical Coherence Tomography, Scheimpflug Imaging, and Ultrasound Pachymetry in Normal, Keratoconus-suspect and Post-laser in situ Keratomileusis Eyes," J. Cataract Refract. Surgery, vol. 35, No. 6, pp. 1055-1062; Jun. 2009 (8 pages).
Proano C.E., et al., "Photochemical Keratodesmos for Bonding Corneal Incisions;" Investigative Ophthalmology & Visual Science, vol. 45, No. 7, pp. 2177-2181; Jul. 2004 (5 pages).
Randall, J. et al., "The Measurementand Intrepretation of Brillouin Scattering in the Lens of the Eye," The Royal Society, Abstract only, published 2013 [available online at http://rspb.royalsocietypublishing.org/content/214/1197/449.short] (1 page).
Reinstein, D. Z. et al. "Epithelial Thickness Profile as a Method to Evaluate the Effectiveness of Collagen Cross-Linking Treatment After Corneal Ectasis." Journal of Refractive Surgery. vol. 27, No. 5, May 2011 (pp. 356-363). [Abstract only].
Reiss, S. et al., "Non-Invasive, ortsaufgeloeste Bestimmung von Gewebeeigenschaften derAugenlinse, Dichte undProteinkonzentration unter Anwendung der Brillouin-spektroskopie", Klin Monatsbl Augenheilkd, vol. 228, No. 12, pp. 1079-1085, Dec. 13, 2011 (7 pages).
Reiss, S. et al., "Spatially resolved Brillouin Spectroscopy to determine the rheological properties of the eye lens", Biomedical Optics Express, vol. 2, No. 8, p. 2144, Aug. 1, 2011 (1 page).
Rocha K., et al., "Comparative Study of Riboflavin-UVA Cross-linking and "Flash-linking" Using Surface Wave Elastometry," Journal of Refractive Surgery, vol. 24 Issue 7, pp. S748-S751; Sep. 2008 (4 pages).
Rolandi et al., "Correlation of Collagen-Linked Fluorescence and Tendon Fiber Breaking Time." Gerontology 1991;27:240-243 (4 pages).
RxList: "Definity Drug Description;" The Internet Drug Index, revised Jun. 16, 2008, retrieved from http://www.rxlist.com/definity-drug.htm, on Sep. 26, 2011 (4 pages).
Saleh et al. "Fundamentals of Photonics" 1991, pp. 74-77.
Scarcelli, G. et al., "Brillouin Optical Microscopy for Corneal Biomechanics", Investigative Ophthalmology & Visual Science, Jan. 2012, vol. 53, No. 1, pp. 185-190 (6 pages).
Sheehan M., et al., "Illumination System for Corneal Collagen Crosslinking," Optometry and Vision Science, vol. 88, No. 4, pp. 512-524; Apr. 2011 (13 pages).
Shell, J., "Pharmacokinetics of Topically Applied Ophthalmic Drugs," Survey of Ophthalmology, vol. 26, No. 4, pp. 207-218; Jan.-Feb. 1982 (12 pages).
Sobol E N et al, "Correction of Eye Refraction by Nonablative Laser Action on Thermomechanical Properties of Cornea and Sclera", Quantum Electronics, Turpion Ltd., London, GB, (Oct. 2002), vol. 32, No. 10, ISSN 1063-7818, pp. 909-912, XP001170947 [A] 1.
Song P., Metzler D. "Photochemical Degradation of Flavins—IV. Studies of the Anaerobic Photolysis of Riboflavin." Photochemistry and Photobiology, vol. 6, pp. 691-709, 1967 (21 pages).
Sonoda S., "Gene Transfer to Corneal Epithelium and Keratocytes Mediated by Ultrasound with Microbubbles," Investigative Ophthalmology & Visual Science, vol. 47, No. 2, pp. 558-564; Feb. 2006 (7 pages).
Spoerl E., et al., "Artificial Stiffening of the Cornea by Induction of Intrastromal Cross-links," Der Ophthalmologe, vol. 94, No. 12, pp. 902-906; Dec. 1997 (5 pages).
Spoerl E., et al., "Induction of Cross-links in Corneal Tissue," Experimental Eye Research, vol. 66, Issue 1, pp. 97-103; Jan. 1998 (7 pages).
Spoerl E. et al., "Safety of UVA-Riboflavin Cross-Linking of the Cornea," Cornea, vol. 26, No. 4, pp. 385-389; May 2007 (5 pages).

(56) References Cited

OTHER PUBLICATIONS

Spoerl E., et al., "Techniques for Stiffening the Cornea," Journal of Refractive Surgery, vol. 15, Issue 6, pp. 711-713; Nov.-Dec. 1999 (4 pages).
Sun, G.J. et al., Abstract for "Properties of 2,3-butanedione and 1-phenyl-1,2-propanedione as new photosensitizers for visible light cured dental resin composites", Polymer 41, pp. 6205-6212, published in 2000 (1 page).
"Tahzib N.G. et al., ""Recurrent intraocular inflamation after implantation of the Artiflex phakic intraocular lens for the correction of high myopia,"" J Cataract Refract Surg, Aug. 2006; 32(8)1388-91, (abstract) [online] [Retrived Mar. 4, 2013] Retrieved from PubMed, PMID: 16863981".
Tessier FJ, et al., "Rigidilication of Corneas Treated in vitro with Glyceraldehyde: Characterization of Two Novel Crosslinks and Two Chromophores," Investigative Opthalmology & Visual Science, vol. 43, E-Abstract; 2002 (2 pages).
Thornton, I. et. al., "Biomechancial Effects of Intraocular Pressure Elevation on Optic Berve/Lamina Cribrosa before and after Peripapillary Scleral Collagen Cross-Linking." Invest. Ophthalm,ol. Vis. Sci., Mar. 2009, 50(3): pp. 1227-1233.
Thornton et al (Investigative Ophthalmology and Visual Science, Mar. 2009, vol. 50, No. 3, pp. 1227-1233).
Tomlinson, A. "Tear Film Osmolarity: Determination of a Referent for Dry Eye Diagnosis", Investigative Ophthalmology & Visual Science, Oct. 2006, vol. 47, No. 10, pp. 4309-4315 (7 pages).
Tomlinson et al. (Investigative Opthalmology and Visual Science 2006, 47 (10), 4309, 4315.
Trembly et al., "Microwave Thermal Keratoplasty for Myopia: Keratoscopic Evaluation in Porcine Eyes," Journal of Refractive Surgery, vol. 17, No. 6, pp. 682-688; Nov./Dec. 2001 (8 pages).
Turgunbaev N.A. et al. Fotomodifikatsiya sklery u bolnykh s progressiruyuschei blizorukostyu (predvaritelnoe soobschenie). 2010 [online]. Retrieved from the Internet:<URL: http://www.eyepress.ru/article.aspx?7484> (2 pages).
"UV-X: Radiation System for Treatment of Keratokonus," PESCHKE Meditrade GmbH; retrieved from http://www.peschkemed.ch/ on Sep. 27, 2011 (date unknown, prior to Sep. 16, 2008) (1 page).
Vasan S., et al., "An agent cleaving glucose-derived protein crosslinks in vitro and in vivo;" Letters to Nature, vol. 382, pp. 275-278; Jul. 18, 1996 (4 pages).
Verzijl et al. Crosslinking by Advanced Glycation End Products Increases the Stiffness of the Collagen Network in Human Articular Cartilage. Arthritis & Rheumatism vol. 46, No. 1, Jan. 2002, pp. 114-123 (10 pages).
Wollensak G., et al., "Biomechanical and Histological Changes After Corneal Crosslinking With and Without Epithelial Debridement," J. Cataract Refract. Surg., vol. 35, Issue 3, pp. 540-546; Mar. 2009 (7 pages).
Wollensak G., et al., "Collagen Crosslinking of Human and Porcine Sclera," J. Cataract Refract. Surg., vol. 30, Issue 3, pp. 689-695; Mar. 2004 (7 pages).
International Search Report issued in co-pending International Application No. PCT/US2016/033718, ISA/RU, dated Sep. 1, 2016, 2 pages.
Written Opinion issued in co-pending International Application No. PCT/US2016/033718, ISA/RU, dated Sep. 1, 2016, 3 pages.
Wollensak G., et al., "Cross-linking of Scleral Collagen in the Rabbit Using Riboflavin and UVA," Acta Ophtalmologica Scandinavica, vol. 83(4), pp. 477-482; Aug. 2005 (6 pages).
Wollensak G., "Crosslinking Treatment of Progressive Keratoconus: New Hope," Current Opinion in Ophthalmology, vol. 17(4), pp. 356-360; Aug. 2006 (5 pages).
Wollensak G., et al., "Hydration Behavior of Porcine Cornea Crosslinked with Riboflavin and Ultraviolet," A.J. Cataract Refract. Surg., vol. 33, Issue 3, pp. 516-521; Mar. 2007 (6 pages).
Wollensak G., et al., "Riboflavin/Ultraviolet-A-induced Collagen Crosslinking for the Treatment of Keratoconus," American Journal of Ophthalmology, vol. 135, No. 5, pp. 620-627; May 2003 (8 pages).
Wollensak, G. et al. "Laboratory Science: Stress-Strain Measurements of Human and Porcine Corneas after Riboflavin-Ultraviolet-A-Induced Cross-Linking." Journal of Cataract and Refractive Surgery. vol. 29, No. 9, Sep. 2003 (pp. 1780-1785).
Wong, J. et al., "Post-Lasik ectasia: PRK following previous stablization and effective management with Riboflavin / ultraviolet A-induced collagen cross-linking," Association for Research in Vision and Ophthalmology, 2006 (1 page).
Yang H., et al., "3-D Histomorphometry of the Normal and Early Glaucomatous Monkey Optic Nerve Head: Lamina Cribrosa and Peripapillary Scleral Position and Thickness," Investigative Ophthalmology & Visual Science, vol. 48, No. 10, pp. 4597-4607; Oct. 2007 (11 pages).
Yang N., Oster G. Dye-sensitized photopolymerization in the presence of reversible oxygen carriers. J. Phys. Chem. 74, 856-860 (1970) (5 pages).
Zhang, Y. et al., "Effect of the Synthetic NC-1059 Peptide on Diffusion of Riboflavin Across an Intact Corneal Epithelium", May 6, 2012, ARBO 2012 Annual Meeting Abstract, 140 Stroma and Keratocytes, program No. 1073, poster board No. A109.
Zhang, Y. et al., "Effects of Ultraviolet-A and Riboflavin on the Interaction of Collagen and Proteoglycans during Corneal Cross-linking", Journal of Biological Chemistry, vol. 286, No. 15, dated Apr. 15, 2011 (pp. 13011-13022).
Zderic V., et al., "Drug Delivery Into the Eye With the Use of Ultrasound," J. Ultrasound Med, vol. 23(10), pp. 1349-1359; Oct. 2004 (11 pages).
Zderic V., et al., "Ultrasound-enhanced Transcorneal Drug Delivery," Cornea vol. 23, No. 8, pp. 804-811; Nov. 2004 (8 pages).

US 10,028,657 B2

SYSTEMS AND METHODS FOR MONITORING CROSS-LINKING ACTIVITY FOR CORNEAL TREATMENTS

CROSS REFERENCE TO RELATED APPLICATIONS

This application claims priority to, and the benefit of, U.S. Provisional Patent Application No. 62/165,741, filed May 22, 2015, the contents of which are incorporated entirely herein by reference.

BACKGROUND

Field

The present disclosure pertains to systems and methods for treating the eye, and more particularly, to systems and methods for monitoring cross-linking activity in corneal treatments.

Description of Related Art

Cross-linking treatments may be employed to treat eyes suffering from disorders, such as keratoconus. In particular, keratoconus is a degenerative disorder of the eye in which structural changes within the cornea cause it to weaken and change to an abnormal conical shape. Cross-linking treatments can strengthen and stabilize areas weakened by keratoconus and prevent undesired shape changes.

Cross-linking treatments may also be employed after surgical procedures, such as Laser-Assisted in situ Keratomileusis (LASIK) surgery. For instance, a complication known as post-LASIK ectasia may occur due to the thinning and weakening of the cornea caused by LASIK surgery. In post-LASIK ectasia, the cornea experiences progressive steepening (bulging). Accordingly, cross-linking treatments can strengthen and stabilize the structure of the cornea after LASIK surgery and prevent post-LASIK ectasia.

SUMMARY

A system for treatment of corneal tissue includes one or more light sources configured to generate excitation light delivered to corneal tissue treated with a cross-linking agent. The excitation light causes the cross-linking agent to fluoresce by emitting an emission light at a plurality of emission wavelengths. The system includes an image capture system configured to capture one or more images of the corneal tissue in response to the delivery of the excitation light to the corneal tissue. The one or more images indicate at least two of the emission wavelengths of the emission light. The system includes a controller configured to receive the one or more images of the corneal tissue. The controller includes one or more processors and computer-readable storage media. The one or more processors are configured to execute program instructions stored on the computer-readable storage media to: identify each of the at least two emission wavelengths in the one or more images; determine, from the one or more images, respective characteristics associated separately with each of the at least two emission wavelengths; and provide information relating to cross-linking activity generated by the cross-linking agent in the corneal tissue based on the respective characteristics associated with each of the at least two emission wavelengths.

A method for treatment of corneal tissue includes delivering, from one or more light sources, excitation light to corneal tissue treated with a cross-linking agent. The excitation light causes the cross-linking agent to fluoresce by emitting an emission light at a plurality of emission wavelengths. The method includes capturing, with an image capture system, one or more images of the corneal tissue in response to the delivery of the excitation light to the corneal tissue. The one or more images indicating at least two of the emission wavelengths of the emission light. The method includes identifying each of the at least two emission wavelengths in the one or more images. The method includes determining, from the one or more images, respective characteristics associated separately with each of the at least two emission wavelengths. The method includes providing information relating to cross-linking activity generated by the cross-linking agent in the corneal tissue based on the respective characteristics associated with each of the at least two emission wavelengths.

DETAILED DESCRIPTION

Figure 1:
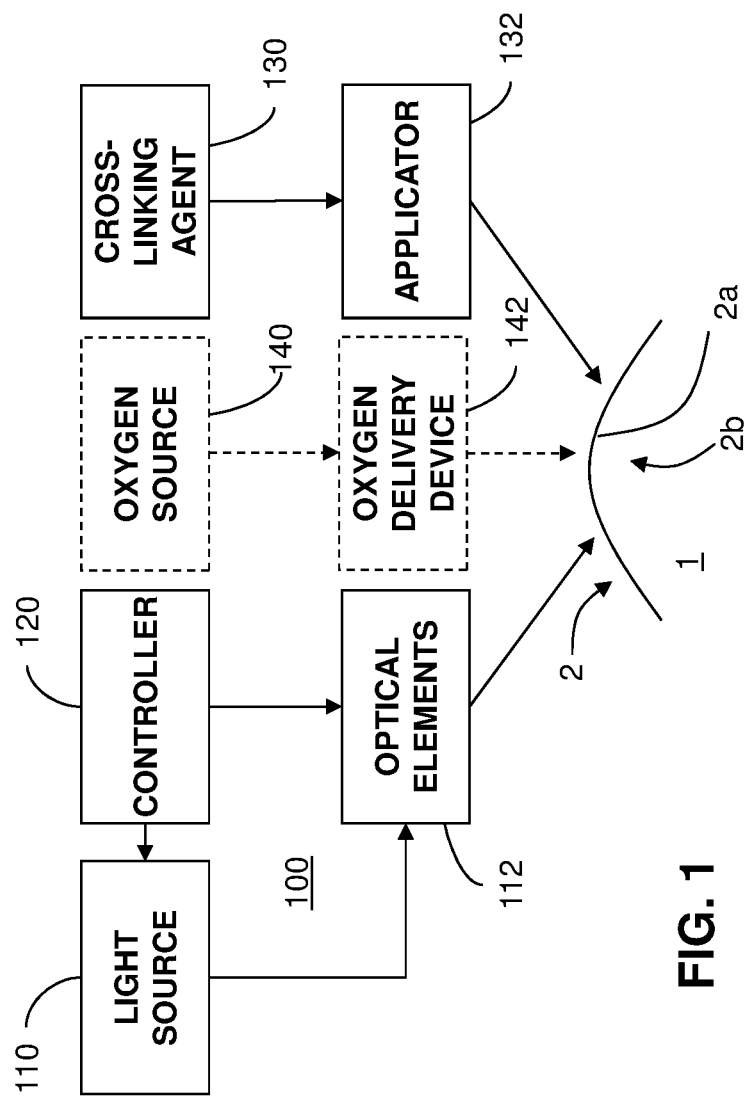
FIG. 1 illustrates an example system that delivers a cross-linking agent and photoactivating light to a cornea of an eye in order to generate cross-linking of corneal collagen, according to aspects of the present disclosure.

FIG. 1 illustrates an example treatment system 100 for generating cross-linking of collagen in a cornea 2 of an eye 1. The treatment system 100 includes an applicator 132 for applying a cross-linking agent 130 to the cornea 2. In example embodiments, the applicator 132 may be an eye dropper, syringe, or the like that applies the photosensitizer 130 as drops to the cornea 2. The cross-linking agent 130 may be provided in a formulation that allows the cross-linking agent 130 to pass through the corneal epithelium 2a and to underlying regions in the corneal stroma 2b. Alternatively, the corneal epithelium 2a may be removed or otherwise incised to allow the cross-linking agent 130 to be applied more directly to the underlying tissue.

The treatment system 100 includes an illumination system with a light source 110 and optical elements 112 for directing light to the cornea 2. The light causes photoactivation of the cross-linking agent 130 to generate cross-linking activity in the cornea 2. For example, the cross-linking agent may include riboflavin and the photoactivating light may include ultraviolet A (UVA) (e.g., approximately 365 nm) light. Alternatively, the photoactivating light may include another wavelength, such as a visible wavelength (e.g., approximately 452 nm). As described further below, corneal cross-linking improves corneal strength by creating chemical bonds within the corneal tissue according to a system of photochemical kinetic reactions. For instance, riboflavin and the photoactivating light may be applied to stabilize and/or strengthen corneal tissue to address diseases such as keratoconus or post-LASIK ectasia.

The treatment system 100 includes one or more controllers 120 that control aspects of the system 100, including the light source 110 and/or the optical elements 112. In an implementation, the cornea 2 can be more broadly treated with the cross-linking agent 130 (e.g., with an eye dropper, syringe, etc.), and the photoactivating light from the light source 110 can be selectively directed to regions of the treated cornea 2 according to a particular pattern.

The optical elements 112 may include one or more mirrors or lenses for directing and focusing the photoactivating light emitted by the light source 110 to a particular pattern on the cornea 2. The optical elements 112 may further include filters for partially blocking wavelengths of light emitted by the light source 110 and for selecting particular wavelengths of light to be directed to the cornea 2 for photoactivating the cross-linking agent 130. In addition, the optical elements 112 may include one or more beam splitters for dividing a beam of light emitted by the light source 110, and may include one or more heat sinks for absorbing light emitted by the light source 110. The optical elements 112 may also accurately and precisely focus the photo-activating light to particular focal planes within the cornea 2, e.g., at a particular depths in the underlying region 2b where cross-linking activity is desired.

Moreover, specific regimes of the photoactivating light can be modulated to achieve a desired degree of cross-linking in the selected regions of the cornea 2. The one or more controllers 120 may be used to control the operation of the light source 110 and/or the optical elements 112 to precisely deliver the photoactivating light according to any combination of: wavelength, bandwidth, intensity, power, location, depth of penetration, and/or duration of treatment (the duration of the exposure cycle, the dark cycle, and the ratio of the exposure cycle to the dark cycle duration).

The parameters for photoactivation of the cross-linking agent 130 can be adjusted, for example, to reduce the amount of time required to achieve the desired cross-linking. In an example implementation, the time can be reduced from minutes to seconds. While some configurations may apply the photoactivating light at an irradiance of 5 mW/cm$^2$, larger irradiance of the photoactivating light, e.g., multiples of 5 mW/cm$^2$, can be applied to reduce the time required to achieve the desired cross-linking. The total dose of energy absorbed in the cornea 2 can be described as an effective dose, which is an amount of energy absorbed through an area of the corneal epithelium 2a. For example the effective dose for a region of the corneal surface 2A can be, for example, 5 J/cm$^2$, or as high as 20 J/cm$^2$ or 30 J/cm$^2$. The effective dose described can be delivered from a single application of energy, or from repeated applications of energy.

The optical elements 112 of the treatment system 100 may include a digital micro-mirror device (DMD) to modulate the application of photoactivating light spatially and temporally. Using DMD technology, the photoactivating light from the light source 110 is projected in a precise spatial pattern that is created by microscopically small mirrors laid out in a matrix on a semiconductor chip. Each mirror represents one or more pixels in the pattern of projected light. With the DMD one can perform topography guided cross-linking. The control of the DMD according to topography may employ several different spatial and temporal irradiance and dose profiles. These spatial and temporal dose profiles may be created using continuous wave illumination but may also be modulated via pulsed illumination by pulsing the illumination source under varying frequency and duty cycle regimes as described above. Alternatively, the DMD can modulate different frequencies and duty cycles on a pixel by pixel basis to give ultimate flexibility using continuous wave illumination. Or alternatively, both pulsed illumination and modulated DMD frequency and duty cycle combinations may be combined. This allows for specific amounts of spatially determined corneal cross-linking. This spatially determined cross-linking may be combined with dosimetry, interferometry, optical coherence tomography (OCT), corneal topography, etc., for pre-treatment planning and/or real-time monitoring and modulation of corneal cross-linking during treatment. Aspects of a dosimetry system are described in further detail below. Additionally, pre-clinical patient information may be combined with finite element biomechanical computer modeling to create patient specific pre-treatment plans.

To control aspects of the delivery of the photoactivating light, embodiments may also employ aspects of multiphoton excitation microscopy. In particular, rather than delivering a single photon of a particular wavelength to the cornea 2, the treatment system 100 may deliver multiple photons of longer wavelengths, i.e., lower energy, that combine to initiate the cross-linking. Advantageously, longer wavelengths are scattered within the cornea 2 to a lesser degree than shorter wavelengths, which allows longer wavelengths of light to penetrate the cornea 2 more efficiently than light of shorter wavelengths. Shielding effects of incident irradiation at deeper depths within the cornea are also reduced over conventional short wavelength illumination since the absorption of the light by the photosensitizer is much less at the longer wavelengths. This allows for enhanced control over depth specific cross-linking. For example, in some embodiments, two photons may be employed, where each photon carries approximately half the energy necessary to excite the molecules in the cross-linking agent 130 to generate the photochemical kinetic reactions described further below. When a cross-linking agent molecule simultaneously absorbs both photons, it absorbs enough energy to release reactive radicals in the corneal tissue. Embodiments may also utilize lower energy photons such that a cross-linking agent molecule must simultaneously absorb, for example, three, four, or five, photons to release a reactive radical. The probability of the near-simultaneous absorption of multiple photons is low, so a high flux of excitation photons may be required, and the high flux may be delivered through a femtosecond laser.

A large number of conditions and parameters affect the cross-linking of corneal collagen with the cross-linking agent 130. For example, the irradiance and the dose of photoactivating light affect the amount and the rate of cross-linking.

When the cross-linking agent 130 is riboflavin in particular, the UVA light may be applied continuously (continuous wave (CW)) or as pulsed light, and this selection has an effect on the amount, the rate, and the extent of cross-linking. If the UVA light is applied as pulsed light, the duration of the exposure cycle, the dark cycle, and the ratio of the exposure cycle to the dark cycle duration have an effect on the resulting corneal stiffening. Pulsed light illumination can be used to create greater or lesser stiffening of corneal tissue than may be achieved with continuous wave illumination for the same amount or dose of energy delivered. Light pulses of suitable length and frequency may be used to achieve more optimal chemical amplification. For pulsed light treatment, the on/off duty cycle may be between approximately 1000/1 to approximately 1/1000; the irradiance may be between approximately 1 mW/cm$^2$ to approximately 1000 mW/cm$^2$ average irradiance, and the pulse rate may be between approximately 0.01 HZ to approximately 1000 Hz or between approximately 1000 Hz to approximately 100,000 Hz.

The treatment system 100 may generate pulsed light by employing a DMD, electronically turning the light source 110 on and off, and/or using a mechanical or opto-electronic (e.g., Pockels cells) shutter or mechanical chopper or rotating aperture. Because of the pixel specific modulation capabilities of the DMD and the subsequent stiffness impartment based on the modulated frequency, duty cycle, irradiance and dose delivered to the cornea, complex biomechanical stiffness patterns may be imparted to the cornea to allow for various amounts of refractive correction. These refractive corrections, for instance, may involve combinations of myopia, hyperopia, astigmatism, irregular astigmatism, presbyopia and complex corneal refractive surface corrections because of ophthalmic conditions such as keratoconus, pellucid marginal disease, post-LASIK ectasia, and other conditions of corneal biomechanical alteration/degeneration, etc. A specific advantage of the DMD system and method is that it allows for randomized asynchronous pulsed topographic patterning, creating a non-periodic and uniformly appearing illumination which eliminates the possibility for triggering photosensitive epileptic seizures or flicker vertigo for pulsed frequencies between 2 Hz and 84 Hz.

Although example embodiments may employ stepwise on/off pulsed light functions, it is understood that other functions for applying light to the cornea may be employed to achieve similar effects. For example, light may be applied to the cornea according to a sinusoidal function, sawtooth function, or other complex functions or curves, or any combination of functions or curves. Indeed, it is understood that the function may be substantially stepwise where there may be more gradual transitions between on/off values. In addition, it is understood that irradiance does not have to decrease down to a value of zero during the off cycle, and may be above zero during the off cycle. Desired effects may be achieved by applying light to the cornea according to a curve varying irradiance between two or more values.

Examples of systems and methods for delivering photoactivating light are described, for example, in U.S. Patent Application Publication No. 2011/0237999, filed Mar. 18, 2011 and titled "Systems and Methods for Applying and Monitoring Eye Therapy," U.S. Patent Application Publication No. 2012/0215155, filed Apr. 3, 2012 and titled "Systems and Methods for Applying and Monitoring Eye Therapy," and U.S. Patent Application Publication No. 2013/0245536, filed Mar. 15, 2013 and titled "Systems and Methods for Corneal Cross-Linking with Pulsed Light," the contents of these applications being incorporated entirely herein by reference.

The addition of oxygen also affects the amount of corneal stiffening. In human tissue, $O_2$ content is very low compared to the atmosphere. The rate of cross-linking in the cornea, however, is related to the concentration of $O_2$ when it is irradiated with photoactivating light. Therefore, it may be advantageous to increase or decrease the concentration of $O_2$ actively during irradiation to control the rate of cross-linking until a desired amount of cross-linking is achieved. Oxygen may be applied during the cross-linking treatments in a number of different ways. One approach involves supersaturating the riboflavin with $O_2$. Thus, when the riboflavin is applied to the eye, a higher concentration of $O_2$ is delivered directly into the cornea with the riboflavin and affects the reactions involving $O_2$ when the riboflavin is exposed to the photoactivating light. According to another approach, a steady state of $O_2$ (at a selected concentration) may be maintained at the surface of the cornea to expose the cornea to a selected amount of $O_2$ and cause $O_2$ to enter the cornea. As shown in FIG. 1, for instance, the treatment system 100 also includes an oxygen source 140 and an oxygen delivery device 142 that optionally delivers oxygen at a selected concentration to the cornea 2. Example systems and methods for applying oxygen during cross-linking treatments are described, for example, in U.S. Pat. No. 8,574,277, filed Oct. 21, 2010 and titled "Eye Therapy," U.S. Patent Application Publication No. 2013/0060187, filed Oct. 31, 2012 and titled "Systems and Methods for Corneal Cross-Linking with Pulsed Light," the contents of these applications being incorporated entirely herein by reference.

When riboflavin absorbs radiant energy, especially light, it undergoes photoactivation. There are two photochemical kinetic pathways for riboflavin photoactivation, Type I and Type II. Some of the reactions involved in both the Type I and Type II mechanisms are as follows:

Common Reactions:

 (r1)

 (r2)

 (r3)

Type I Reactions:

 (r4)

 (r5)

Type II Reactions:

 (r6)

 (r7)

 (r8)

In the reactions described herein, Rf represents riboflavin in the ground state. $Rf^*_1$ represents riboflavin in the excited singlet state. $Rf^*_3$ represents riboflavin in a triplet excited state. $Rf.^-$ is the reduced radical anion form of riboflavin. RfH. is the radical form of riboflavin. $RfH_2$ is the reduced form of riboflavin. DH is the substrate. $DH.^+$ is the intermediate radical cation. D. is the radical. $D_{ox}$ is the oxidized form of the substrate.

Riboflavin is excited into its triplet excited state $Rf^*_3$ as shown in reactions (r1) to (r3). From the triplet excited state Rf*$_3$, the riboflavin reacts further, generally according to Type I or Type II mechanisms. In the Type I mechanism, the substrate reacts with the excited state riboflavin to generate radicals or radical ions, respectively, by hydrogen atoms or electron transfer. In Type II mechanism, the excited state riboflavin reacts with oxygen to form singlet molecular oxygen. The singlet molecular oxygen then acts on tissue to produce additional cross-linked bonds.

Oxygen concentration in the cornea is modulated by UVA irradiance and temperature and quickly decreases at the beginning of UVA exposure. Utilizing pulsed light of a specific duty cycle, frequency, and irradiance, input from both Type I and Type II photochemical kinetic mechanisms can be employed to achieve a greater amount of photochemical efficiency. Moreover, utilizing pulsed light allows regulating the rate of reactions involving riboflavin. The rate of reactions may either be increased or decreased, as needed, by regulating, one of the parameters such as the irradiance, the dose, the on/off duty cycle, riboflavin concentration, soak time, and others. Moreover, additional ingredients that affect the reaction and cross-linking rates may be added to the cornea.

If UVA radiation is stopped shortly after oxygen depletion, oxygen concentrations start to increase (replenish). Excess oxygen may be detrimental in the corneal cross-linking process because oxygen is able to inhibit free radical photopolymerization reactions by interacting with radical species to form chain-terminating peroxide molecules. The pulse rate, irradiance, dose, and other parameters can be adjusted to achieve a more optimal oxygen regeneration rate. Calculating and adjusting the oxygen regeneration rate is another example of adjusting the reaction parameters to achieve a desired amount of corneal stiffening.

Oxygen content may be depleted throughout the cornea, by various chemical reactions, except for the very thin corneal layer where oxygen diffusion is able to keep up with the kinetics of the reactions. This diffusion-controlled zone will gradually move deeper into the cornea as the reaction ability of the substrate to uptake oxygen decreases.

Riboflavin is reduced (deactivated) reversibly or irreversibly and/or photo-degraded to a greater extent as irradiance increases. Photon optimization can be achieved by allowing reduced riboflavin to return to ground state riboflavin in Type I reactions. The rate of return of reduced riboflavin to ground state in Type I reactions is determined by a number of factors. These factors include, but are not limited to, on/off duty cycle of pulsed light treatment, pulse rate frequency, irradiance, and dose. Moreover, the riboflavin concentration, soak time, and addition of other agents, including oxidizers, affect the rate of oxygen uptake. These and other parameters, including duty cycle, pulse rate frequency, irradiance, and dose can be selected to achieve more optimal photon efficiency and make efficient use of both Type I as well as Type II photochemical kinetic mechanisms for riboflavin photosensitization. Moreover, these parameters can be selected in such a way as to achieve a more optimal chemical amplification effect.

In addition to the photochemical kinetic reactions (r1)-(r8) above, however, the present inventors have identified the following photochemical kinetic reactions (r9)-(r26) that also occur during riboflavin photoactivation:

$$Rf_3^* \rightarrow Rf, \kappa 8; \tag{r9}$$

$$Rf_3^* + Rf \rightarrow 2RfH., \kappa 9; \tag{r10}$$

$$RfH_2 + O_2 \rightarrow RfH.+H^+ + O_2^-, \kappa 10; \tag{r11}$$

$$RfH.+O_2 \rightarrow Rf+H^+ + O_2^-, \kappa 11; \tag{r12}$$

$$2RfH_2 + O_2^- \rightarrow 2RfH.+H_2O_2, \kappa 12; \tag{r13}$$

$$2RfH.+O_2^- \rightarrow 2Rf+H_2O_2, \kappa 13; \tag{r14}$$

$$RfH.+H_2O_2 \rightarrow OH.+Rf+H_2O, \kappa 14; \tag{r15}$$

$$OH.+DH \rightarrow D.+H_2O, \kappa 15; \tag{r16}$$

$$D.+D. \rightarrow D-D, \kappa 16; CXL \tag{r17}$$

$$O_2^1 \rightarrow O_2, k18; \tag{r18}$$

$$D.+RfH_2 \rightarrow RfH.+DH, \kappa 19; \tag{r19}$$

$$Rf + Rf \underset{\kappa_a^-}{\overset{\kappa_a^+}{\rightleftharpoons}} A_1, \quad \kappa_a = \kappa_a^+ / \kappa_a^- \tag{r20}$$

$$RfH_2 + RfH_2 \underset{\kappa_a^-}{\overset{\kappa_a^+}{\rightleftharpoons}} A_2, \quad \kappa_a = \kappa_a^+ / \kappa_a^- \tag{r21}$$

$$Rf + RfH_2 \underset{\kappa_b^-}{\overset{\kappa_b^+}{\rightleftharpoons}} A_3, \quad \kappa_b = \kappa_b^+ / \kappa_b^- \tag{r22}$$

$$Rf_1^* + A \rightarrow Rf + A, \kappa_{1a} \tag{r23}$$

$$Rf_3^* + A \rightarrow Rf + A, \kappa_{3a} \tag{r24}$$

$$2O_2^- \rightarrow O_2 + H_2O_2, \kappa_{12} \tag{r25}$$

$$OH° + CXL \rightarrow \text{inert products}, \kappa_{OH} \tag{r26}$$

Figure 2A:
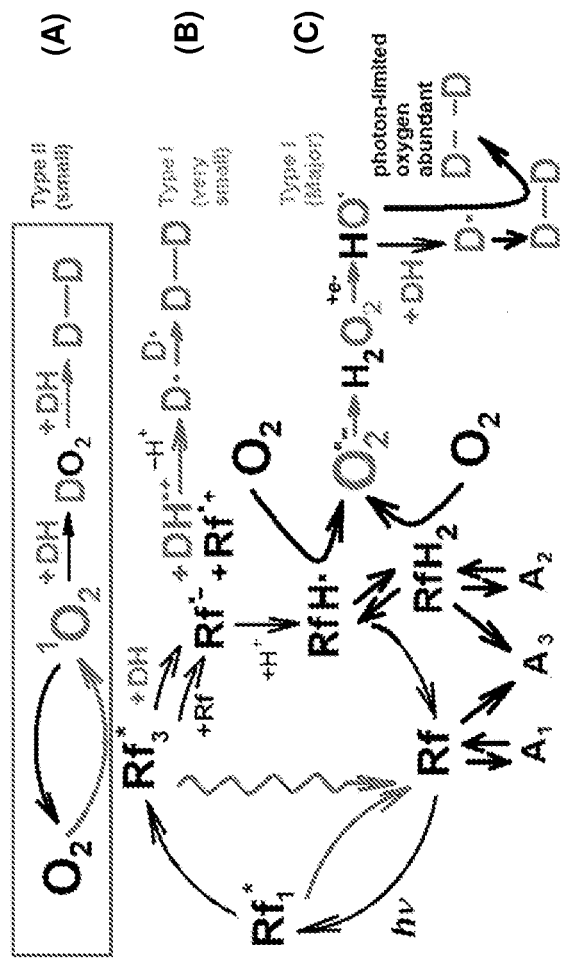
FIG. 2A illustrates a diagram for photochemical kinetic reactions involving riboflavin and photoactivating light (e.g., ultraviolet A (UVA) light) applied during a corneal cross-linking treatment, according to aspects of the present disclosure.

FIG. 2A illustrates a diagram for the photochemical kinetic reactions provided in reactions (r1) through (r26) above. The diagram summarizes photochemical transformations of riboflavin (Rf) under UVA photoactivating light and its interactions with various donors (DH) via electron transfer. As shown, cross-linking activity occurs: (A) through the presence of singlet oxygen in reactions (r6) through (r8) (Type II mechanism); (B) without using oxygen in reactions (r4) and (r17) (Type I mechanism); and (C) through the presence of peroxide ($H_2O_2$), superoxide ($O_2^-$), and hydroxyl radicals (.OH) in reactions (r13) through (r17).

As shown in FIG. 2A, the present inventors have also determined that the cross-linking activity is generated to a greater degree from reactions involving peroxide, superoxide, and hydroxyl radicals. Cross-linking activity is generated to a lesser degree from reactions involving singlet oxygen and from non-oxygen reactions. Some models based on the reactions (r1)-(r26) can account for the level of cross-linking activity generated by the respective reactions. For instance, where singlet oxygen plays a smaller role in generating cross-linking activity, models may be simplified by treating the cross-linking activity resulting from singlet oxygen as a constant.

All the reactions start from Rf$_3$* as provided in reactions (r1)-(r3). The quenching of Rf$_3$* occurs through chemical reaction with ground state Rf in reaction (r10), and through deactivation by the interaction with water in reaction (r9).

As described above, excess oxygen may be detrimental in corneal cross-linking process. As shown in FIG. 2A, when the system becomes photon-limited and oxygen-abundant, cross-links can be broken from further reactions involving superoxide, peroxide, and hydroxyl radicals. Indeed, in some cases, excess oxygen may result in net destruction of cross-links versus generation of cross-links.

As described above, a large variety of factors affect the rate of the cross-linking reaction and the amount of biomechanical stiffness achieved due to cross-linking. A number of these factors are interrelated, such that changing one factor may have an unexpected effect on another factor. However, a more comprehensive model for understanding the relationship between different factors for cross-linking treatment is provided by the photochemical kinetic reactions (r1)-(r26) identified above. Accordingly, systems and methods can adjust various parameters for cross-linking treatment according to this photochemical kinetic cross-linking model, which provides a unified description of oxygen dynamics and cross-linking activity. The model can be employed to evaluate expected outcomes based on different combinations of treatment parameters and to identify the combination of treatment parameters that provides the desired result. The parameters, for example, may include, but are not limited to: the concentration(s) and/or soak times of the applied cross-linking agent; the dose(s), wavelength(s), irradiance(s), duration(s), and/or on/off duty cycle(s) of the photoactivating light; the oxygenation conditions in the tissue; and/or presence of additional agents and solutions.

Figure 2B:
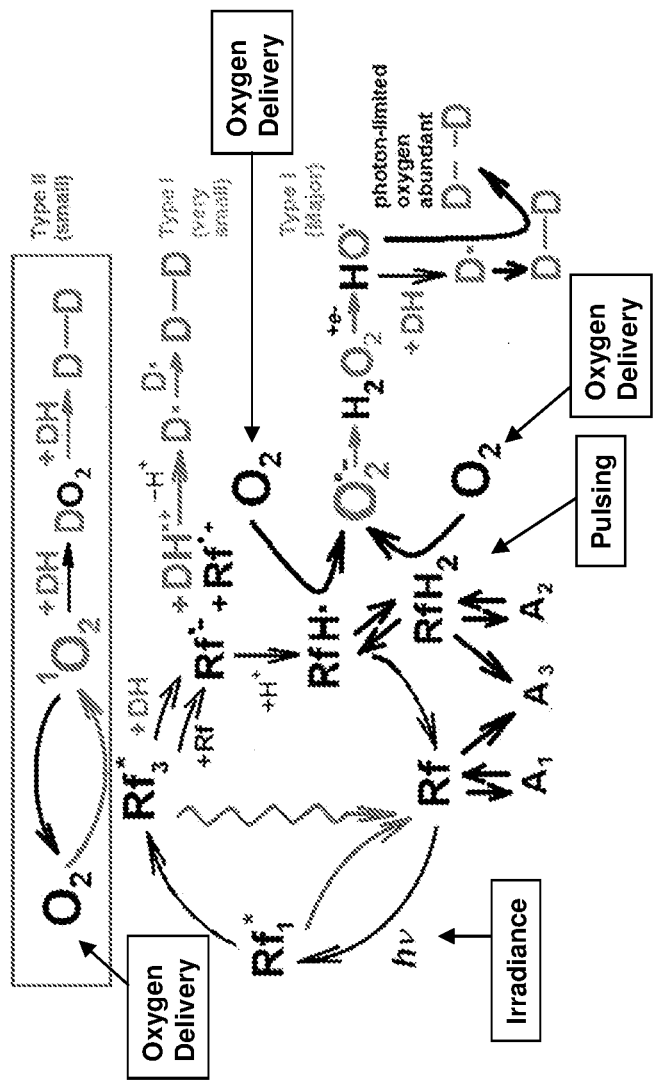
FIG. 2B illustrates a diagram for parameters that can affect the photochemical kinetic reactions shown in FIG. 2A.

As shown in FIG. 2B, aspects of the system of reactions can be affected by different parameters. For instance, the irradiance at which photoactivating light is delivered to the system affects the photons available in the system to generate $Rf_3^*$ for subsequent reactions. Additionally, delivering greater oxygen into the system drives the oxygen-based reactions. Meanwhile, pulsing the photoactivating light affects the ability of the reduced riboflavin to return to ground state riboflavin by allowing additional time for oxygen diffusion. Of course, other parameters can be varied to control the system of reactions.

Figure 3:
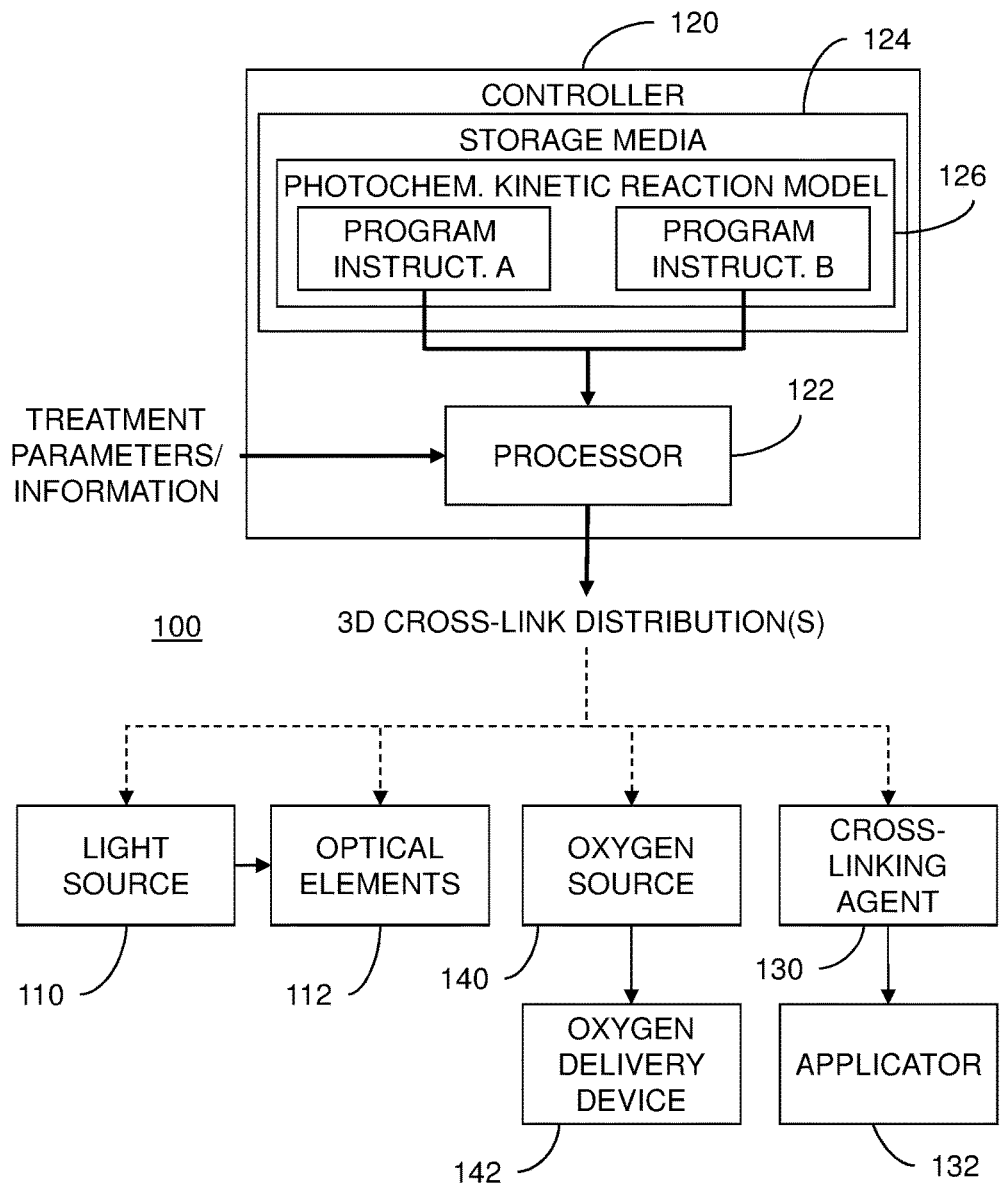
FIG. 3 illustrates an example system employing a model of photochemical kinetic reactions according to aspects of the present disclosure.

According to an embodiment, FIG. 3 illustrates the example system 100 employing a model based on the photochemical kinetic reactions (r1)-(r26) identified above to determine an amount of cross-linking that results from treatment parameters and/or other related information. The controller 120 includes a processor 122 and computer-readable storage media 124. The storage media 124 stores program instructions for determining an amount of cross-linking when the photoactivating light from the light source 110 is delivered to a selected region of a cornea treated with a cross-linking agent. In particular, a photochemical kinetic model 126 based on the reactions (r1)-(r26) may include a first set of program instructions A for determining cross-linking resulting from reactions involving reactive oxygen species (ROS) including combinations of peroxides, superoxides, hydroxyl radicals, and/or singlet oxygen and a second set of program instructions B for determining cross-linking from reactions not involving oxygen. The controller 120 receives input relating to treatment parameters and/or other related information. The controller 120 can then execute the program instructions A and B to output information relating to three-dimensional cross-link distribution(s) for the selected region of the cornea based on the input. The three-dimensional cross-link distribution(s) may then be employed to determine how to control aspects of the light source 110, the optical elements 112, the cross-linking agent 130, the applicator 132, the oxygen source 140, and/or oxygen delivery device 142 in order to achieve a desired treatment in selected region of the cornea. (Of course, the system 100 shown in FIG. 3 and this process can be used for treatment of more than one selected region of the same cornea.)

According to one implementation, the three-dimensional cross-link distribution(s) may be evaluated to calculate a threshold depth corresponding to a healing response due to the cross-links and an effect of the reactive-oxygen species in the selected region of the cornea. Additionally or alternatively, the three-dimensional cross-link distribution(s) may be evaluated to calculate a biomechanical tissue stiffness threshold depth corresponding to a biomechanical tissue response in the selected region of the cornea. The information on the depth of the healing response and/or the biomechanical tissue stiffness in the cornea can be employed to determine how to control aspects of the light source 110, the optical elements 112, the cross-linking agent 130, the applicator 132, the oxygen source 140, and/or oxygen delivery device 142. Certain healing response and/or biomechanical tissue stiffness may be desired or not desired at certain depths of the cornea.

Figure 4:
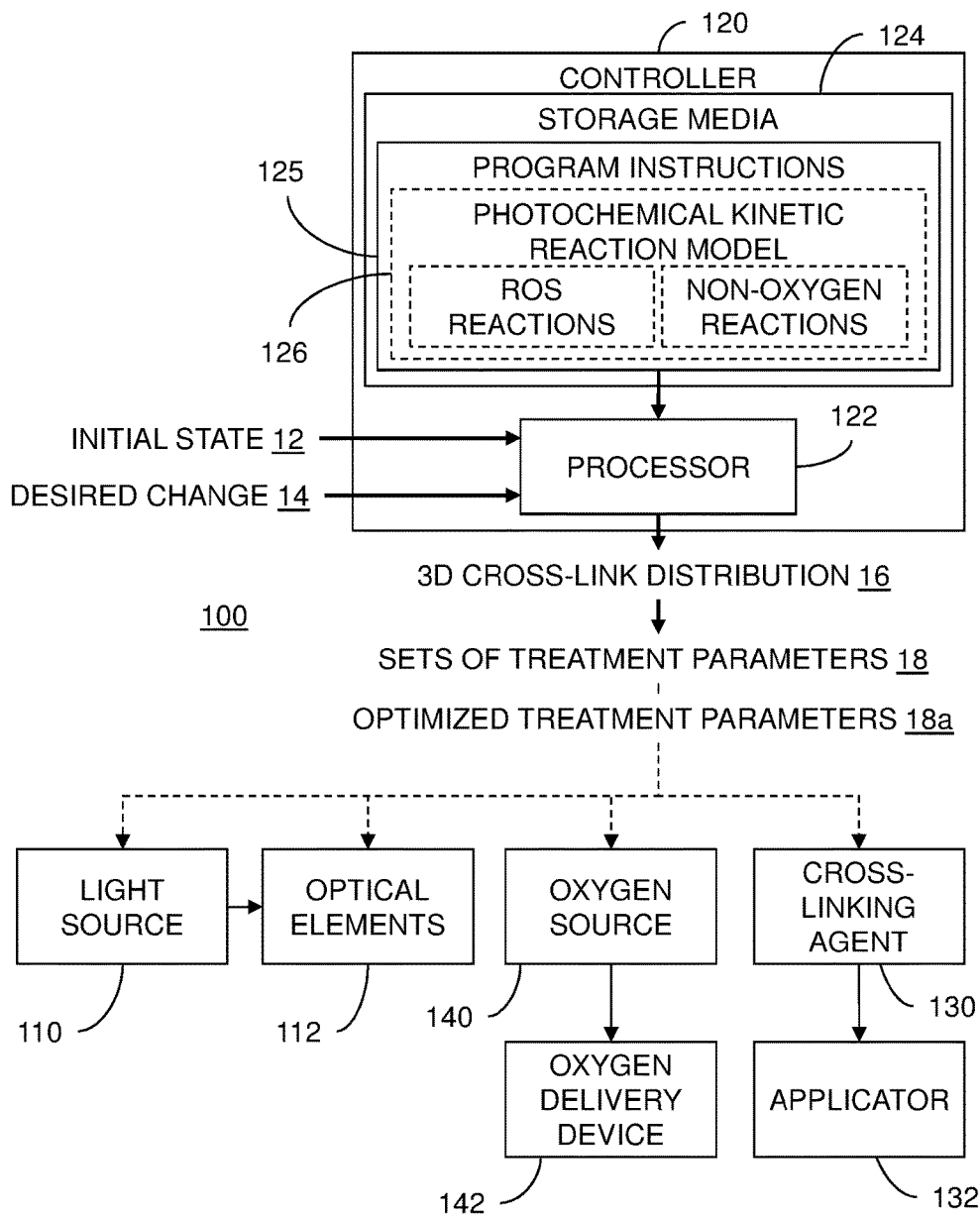
FIG. 4 illustrates an example system employing a model of photochemical kinetic reactions to provide treatment parameters for achieving desired biomechanical changes according to aspects of the present disclosure.

According to another embodiment, FIG. 4 illustrates the example system 100 employing the photochemical kinetic model 126 to determine treatment parameters for achieving desired biomechanical changes in the cornea, e.g., a refractive correction. As in FIG. 3, the controller 120 includes the processor 122 and the computer-readable storage media 124. In the example of FIG. 4, however, the storage media 124 stores program instructions 125 for determining what treatment parameters may be employed to achieve desired biomechanical changes. The program instructions 125 are based on the photochemical kinetic model 126 which employ the reactions (r1)-(r26) to determine cross-linking resulting from (i) reactions involving reactive oxygen species (ROS) including combinations of peroxides, superoxides, hydroxyl radicals, and/or singlet oxygen and (ii) reactions not involving oxygen.

Using the photochemical kinetic model 126, a three-dimensional distribution of resulting cross-links throughout the treated corneal tissue can be determined for a combination of treatment parameters. As described above, parameters for cross-linking treatment may include: the concentration(s) and/or soak times of the applied cross-linking agent; the dose(s), wavelength(s), irradiance(s), duration(s), on/off duty cycle(s), and/or other illumination parameters for the photoactivating light; the oxygenation conditions in the tissue; and/or presence of additional agents and solutions. The resulting distribution of cross-links determined from the photochemical kinetic model 126 can be correlated to a particular biomechanical change in the cornea. For instance, there is a correlation between the distribution of cross-links and refractive change.

As shown in FIG. 4, the controller 120 receives an input 12 relating to the initial biomechanical state of the cornea and an input 14 indicating a desired biomechanical change for the cornea, e.g., for refractive correction. The initial biomechanical state, for instance, can be determined according to approaches described in U.S. Patent Application Publication No. 2012/0215155 referenced above. In some cases, the input 12 may be provided by a measurement system communicatively coupled to the controller 120. It is understood that the initial biomechanical state may reflect the state of the cornea prior to any treatment or during a treatment.

The inputs 12, 14 may be expressed in terms of corneal topography (i.e., shape), corneal strength (i.e., stiffness), and/or corneal thickness. For instance, the desired biomechanical change for refractive correction may be determined from a correction specified (by a practitioner) in diopters, e.g., "a 1.5 diopter correction."

A desired biomechanical change in the cornea can be correlated to a particular distribution of cross-links as determined by the photochemical kinetic model 126. As such, the controller 120 can execute the program instructions 125 to determine the particular distribution of cross-links 16 that can generate the desired biomechanical change specified by the input 14 in a cornea having the initial biomechanical state specified by the input 12. After determining the distribution of cross-links 16 for the desired biomechanical change, the controller 120 can prescribe a set of treatment parameters for achieving the specified distribution of cross-links.

The distribution of cross-links 16 might be achieved in many cases by more than one set of treatment parameters. For instance, depending on the photochemical kinetic reactions, similar distributions of cross-links may be achieved by applying: (i) a lower dose of photoactivating light for a longer amount of time, or (ii) a higher dose of photoactivating light for a shorter amount of time. Therefore, more than one set of treatment parameters 18 for achieving the distribution of cross-links 16 may be identified.

With more than one possible set of treatment parameters 18, a practitioner can optimize the treatment for certain preferred parameters, such as treatment time or dose of photoactivating light. For instance, the practitioner may optimize the treatment parameters to achieve shorter treatment times. For this preference, the controller 120 may prescribe a set of illumination parameters that provide a larger dose of photoactivating light that yields the distribution of cross-links 16 over shorter illumination durations. Conversely, the practitioner may optimize the treatment parameters to employ smaller doses of photoactivating light. For this second preference, the controller 120 may prescribe a set of illumination parameters that provide a smaller dose of photoactivating light that yields the distribution of cross-links 16 over longer illumination durations.

In general, to achieve the distribution of cross-links 16, the controller 120 may identify any of the different combinations 18 of values for a set of treatment parameters A, B, C, D, E, etc., as described above. The practitioner can set preferences for one or more of these treatment parameters. For instance, the practitioner may initially set a preferred value or range of preferred values for parameter A. In response, the controller 120 can specify combinations of values for the remaining parameters B, C, D, E, etc., that meet the preference for parameter A while achieving the distribution of cross-links 16. The practitioner may make selections for the values of the parameters B, C, D, and/or E, etc., based on further preferences to arrive at an optimized set of treatment parameters 18a. The process of optimizing the treatment parameters may be iterative as the values for the treatment parameters are incrementally tuned to meet preferences having varying priorities.

In some embodiments, the practitioner may manage the optimization process through a series of selections and other inputs via a user interface (not shown) coupled to the controller 120. In some cases, the inputs 12, 14 may also be provided through such a user interface.

The final set of treatment parameters 18a can then be employed to determine how to control aspects of the light source 110, the optical elements 112, the cross-linking agent 130, the applicator 132, the oxygen source 140, oxygen delivery device 142, etc., in order to achieve a desired treatment in selected region of the cornea.

Figure 5:
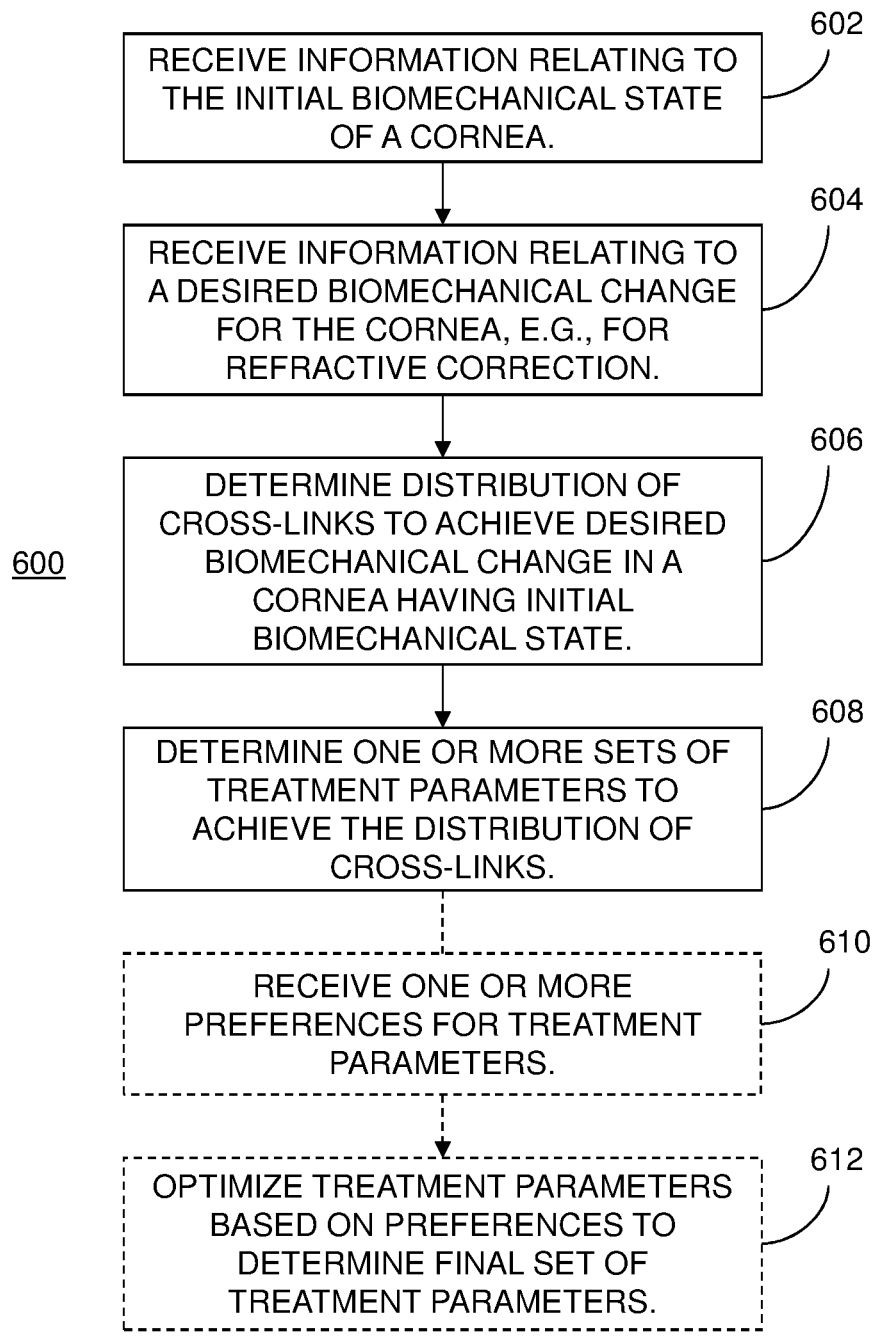
FIG. 5 an example method employing a model of photochemical kinetic reactions to determine treatment parameters for achieving desired biomechanical changes according to aspects of the present disclosure.

Correspondingly, FIG. 5 illustrates an example method 600 for employing a model of photochemical kinetic reactions (r1)-(r26) to determine treatment parameters for achieving desired biomechanical changes. In step 602, information relating to the initial biomechanical state of a cornea is received. In step 604, information relating to a desired biomechanical change for the cornea, e.g., for refractive correction, is received. In step 606, a distribution of cross-links is determined to achieve the desired biomechanical change in a cornea having the initial biomechanical state. In step 608, one or more sets of treatment parameters are determined to achieve the distribution of cross-links. In association with step 608, one or more preferences for treatment parameters may be received in step 610, and the treatment parameters may be optimized in step 612 based on the one or more preferences to determine a final set of treatment parameters that can be implemented in a treatment system (e.g., the example system 100) to achieve the distribution of cross-links.

Further aspects of the photochemical kinetic reactions provided in reactions (r1)-(r26) are described in U.S. patent application Ser. No. 15/140,184, filed Apr. 27, 2016 and titled "Systems and Methods for Cross-Linking Treatments of an Eye," the contents of which are incorporated entirely herein by reference.

When light of a particular wavelength is applied to a cross-linking agent, such as riboflavin, the light can excite the cross-linking agent and cause the cross-linking agent to fluoresce. As such, an excitation light can be employed to cause a cross-linking agent in corneal tissue to fluoresce and determine how the cross-linking agent is distributed in the corneal tissue. When an image of the cornea is taken during the application of the excitation light, the intensity (magnitude) of the fluorescence, for instance, can be measured to determine the amount, i.e., dose, of cross-linking agent taken up by the corneal tissue. Using these principles, dosimetry systems can determine the presence and distribution of the cross-linking agent in the cornea by capturing one or more images of the fluorescence from the cross-linking agent as it responds to the excitation light.

Figure 6:
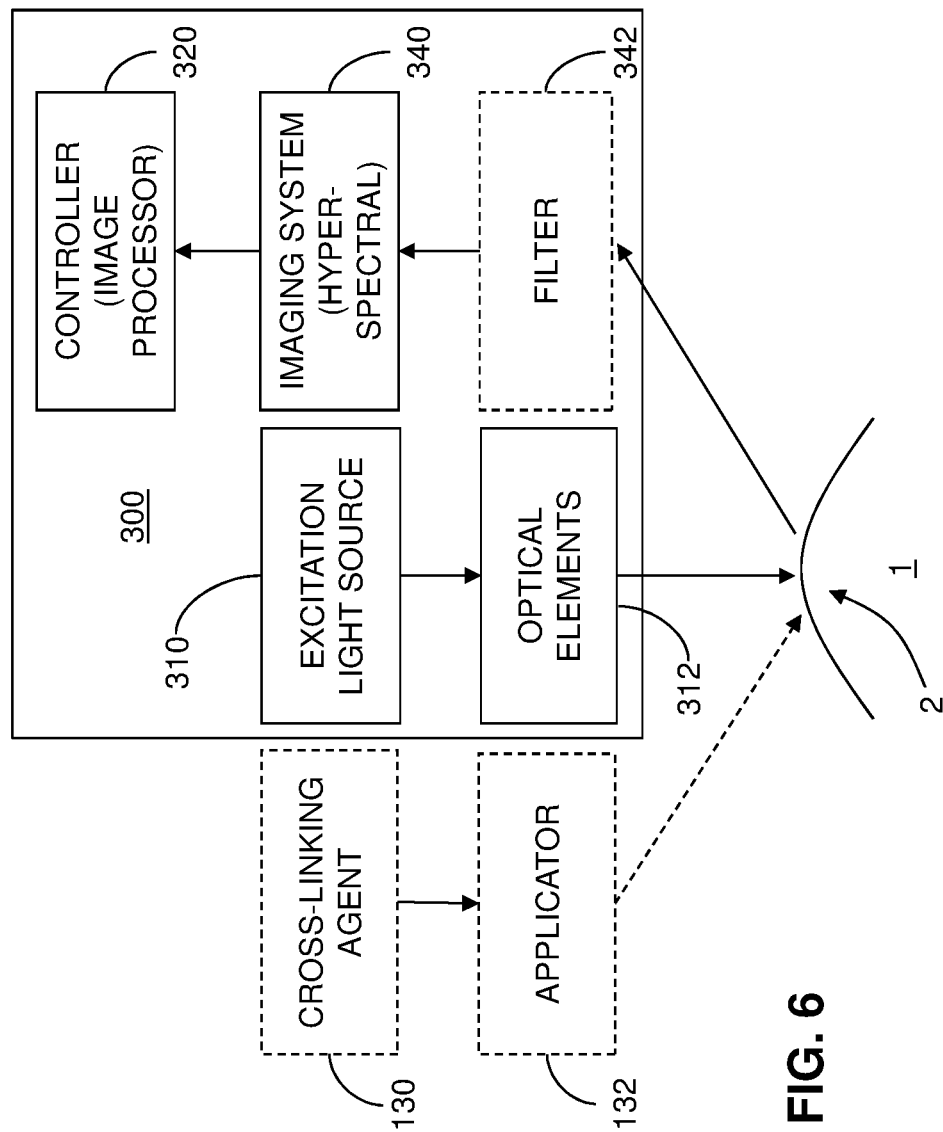
FIG. 6 illustrates an example dosimetry system, according to aspects of the present disclosure.

FIG. 6 illustrates an example dosimetry system 300. The example dosimetry system 300 includes an excitation light source 310 and optical elements 312. As described above, an applicator 132 may be employed to deliver a cross-linking agent 130 to a cornea 2 of an eye 1. The light source 310 provides light that can excite the cross-linking agent 130 in corneal tissue and cause the cross-linking agent 130 to fluoresce.

The optical elements 312 may include mirrors, lenses, apertures, filters, beam splitters, and the like to direct the light from the light source 310 to the cornea 2. The light from the light source 310 may be applied to the cornea 2 according to any combination of: wavelength, spectral bandwidth, intensity, power, location, depth of penetration, waveform, and/or duration of delivery.

Figure 7A:
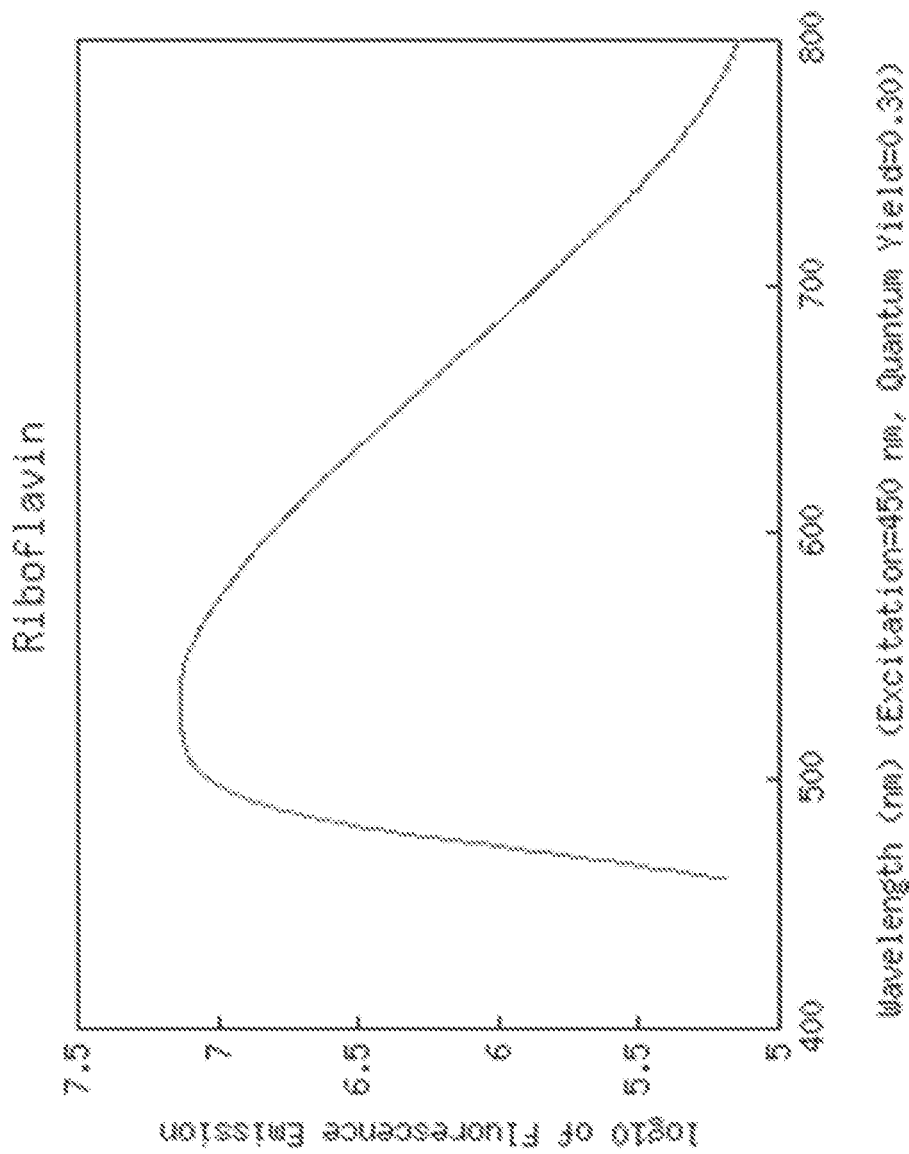
FIG. 7A illustrates an example emission spectrum for riboflavin when excited by light with a wavelength of 450 nm, according to aspects of the present disclosure.

FIG. 7A illustrates an example fluorescence emission spectrum for riboflavin, with a peak wavelength of approximately 525 nm, when the riboflavin is excited by light having a wavelength of approximately 450 nm. Thus, if the cross-linking agent 130 in FIG. 6 includes riboflavin, the light source 310 and optical elements 312 may deliver light having a wavelength of approximately 450 nm to cause the cross-linking agent 130 to fluoresce. In general, however, the light source 310 may be configured to provide light of various wavelengths to cause different types of the cross-linking agents 130 to fluoresce. For instance, the riboflavin may additionally or alternatively be excited by light having a wavelength of approximately 365 nm.

In some embodiments, the light source 310 and the optical elements 312 can additionally apply light that photoactivates the cross-linking agent and generates cross-linking activity in the cornea 2. For instance, if the cross-linking agent 130 is riboflavin, the light source 310 and the optical elements 312 may deliver photoactivating ultraviolet-A (UVA) light to the cornea 2, e.g., with wavelengths ranging from approximately 365 nm to approximately 370 nm.

The example dosimetry system 300 also includes an imaging system 340 for capturing one or more images of the eye 1 while the cross-linking agent 130 fluoresces in response to the excitation light. Additionally, the example dosimetry system 300 includes a controller 320 that processes the one or more images acquired via the imaging system 340. The presence of light at characteristic fluorescence wavelengths of the cross-linking agent 130 in the images indicates the presence and distribution of the cross-linking agent 130 in the cornea 2. Configurations for capturing images with an imaging system are described, for example, in U.S. Pat. No. 9,020,580, filed Jun. 4, 2012, the contents of which are incorporated entirely herein by reference. Information regarding the presence and distribution of the cross-linking agent 130 in the cornea 2 may be electronically communicated from the example dosimetry system 300 to other systems and/or displayed or otherwise presented physically via a user interface.

Figure 7B:
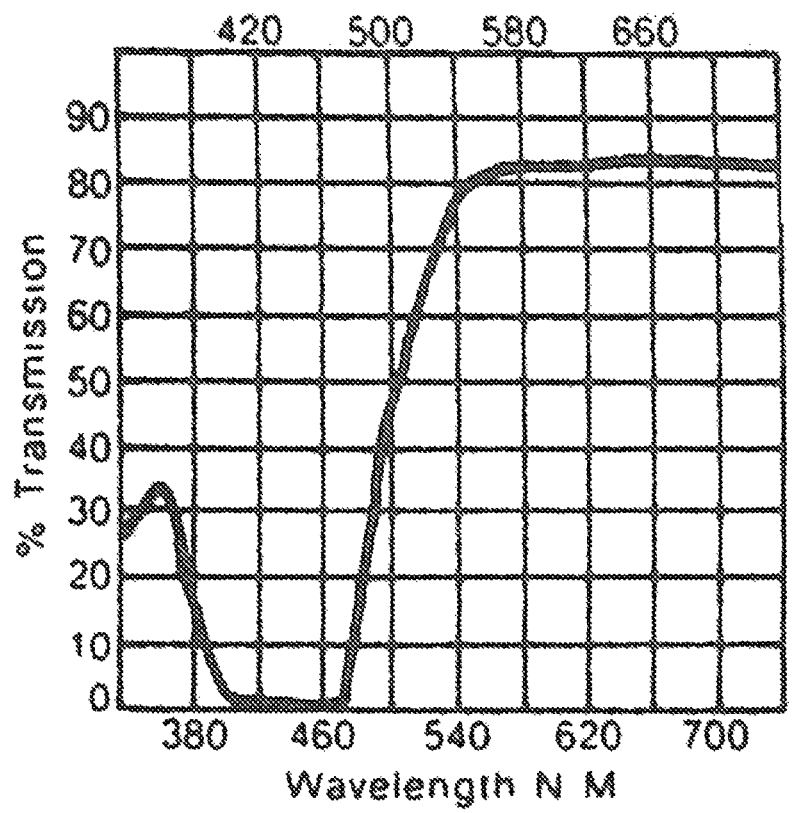
FIG. 7B illustrates an example transmission spectrum when a filter is employed during the excitation of riboflavin by light with a wavelength of 450 nm, according to aspects of the present disclosure.

The example dosimetry system 300 may also include an optional filter 342 to block wavelengths of light from the light source 310. For instance, the filter 342 may employ a configuration of rotating wheel of filters, sliding filters, series of cascading dichroic beam splitters, or the like. With the filter 342, the imaging system 340 captures wavelengths of light emitted from the fluorescing cross-linking agent 130 but not the wavelengths of light from the excitation light system 310. Thus, the filter 342 can improve the signal to noise ratio of the example dosimetry system 300. For example, FIG. 7B illustrates the transmission spectrum with a filter that blocks excitation light having a wavelength of approximately 450 nm light, while allowing the fluorescence emission (with peak wavelength of approximately 525 nm) to reach the imaging system. It is understood, however, that in addition to the fluorescence transmission, the excitation light may produce other effects, such as scattering, that may yield useful information on the cross-linking treatment.

The imaging system 340 can capture cross-sectional images at different depths of the cornea 2, where each image captures the fluorescence emission of the cross-linking agent 130 along a particular cross-section of the cornea 2. For instance, the intensity can be measured for respective cross-sectional portions of the cornea to determine the amount of the cross-linking agent 130 at different depths of the cornea 2. As such, a distribution of the cross-linking agent 130 as a function of depth can be characterized.

The example dosimetry system 300 may be employed to determine the distribution of the cross-linking agent 130 over time and to determine the rate at which the corneal tissue takes up the cross-linking agent 130. In addition, the change in the distribution of the cross-linking agent 130 over time can be used to determine the amount of cross-linking activity that takes place in regions of the corneal tissue.

The rate at which the cross-linking agent 130 is taken up may also be an indicator of different bio-chemical, biomechanical, and/or opto-mechanical properties of the corneal tissue. Furthermore, the rate at which the cross-linking agent 130 is taken up by the corneal tissue may also be an indicator of different pathologies of disease.

As shown in FIG. 6, the example dosimetry system 300 may be combined with the applicator 132 that applies the cross-linking agent 130 to the cornea 2. The applicator 132 may be employed to apply additional doses of the cross-linking agent 130 if the example dosimetry system 300 indicates insufficient dose or distribution of the cross-linking agent 130 in targeted regions of the corneal tissue.

The example dosimetry system 300 may be employed with the example system 100 of FIGS. 3 and 4. The example dosimetry 300 can provide the presence and distribution of the cross-linking agent 130 in the cornea 2 as input (e.g., input 12) to allow the example system 100 to determine a resulting three-dimensional distribution of cross-links and/or to optimize treatment parameters.

Figure 8:
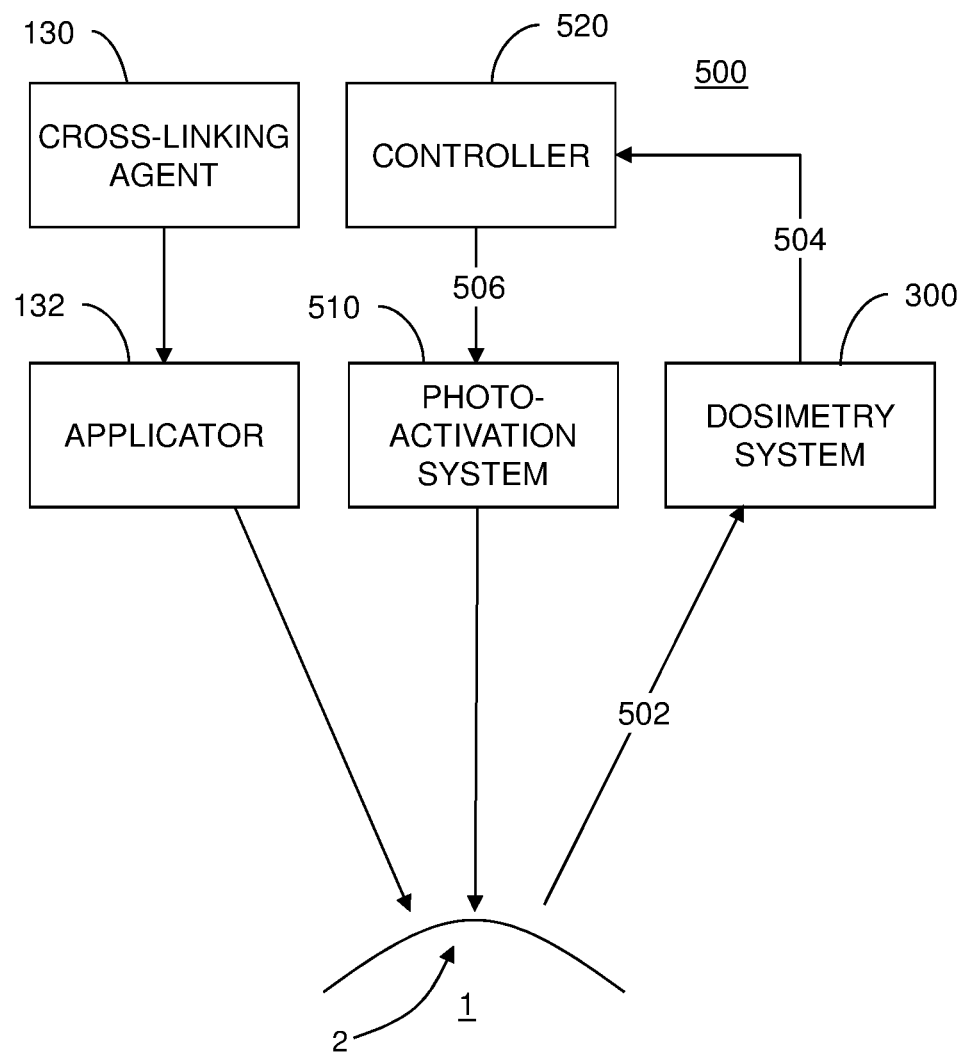
FIG. 8 illustrates an example treatment system including feedback from a dosimetry system, according to aspects of the present disclosure.
Figure 9:
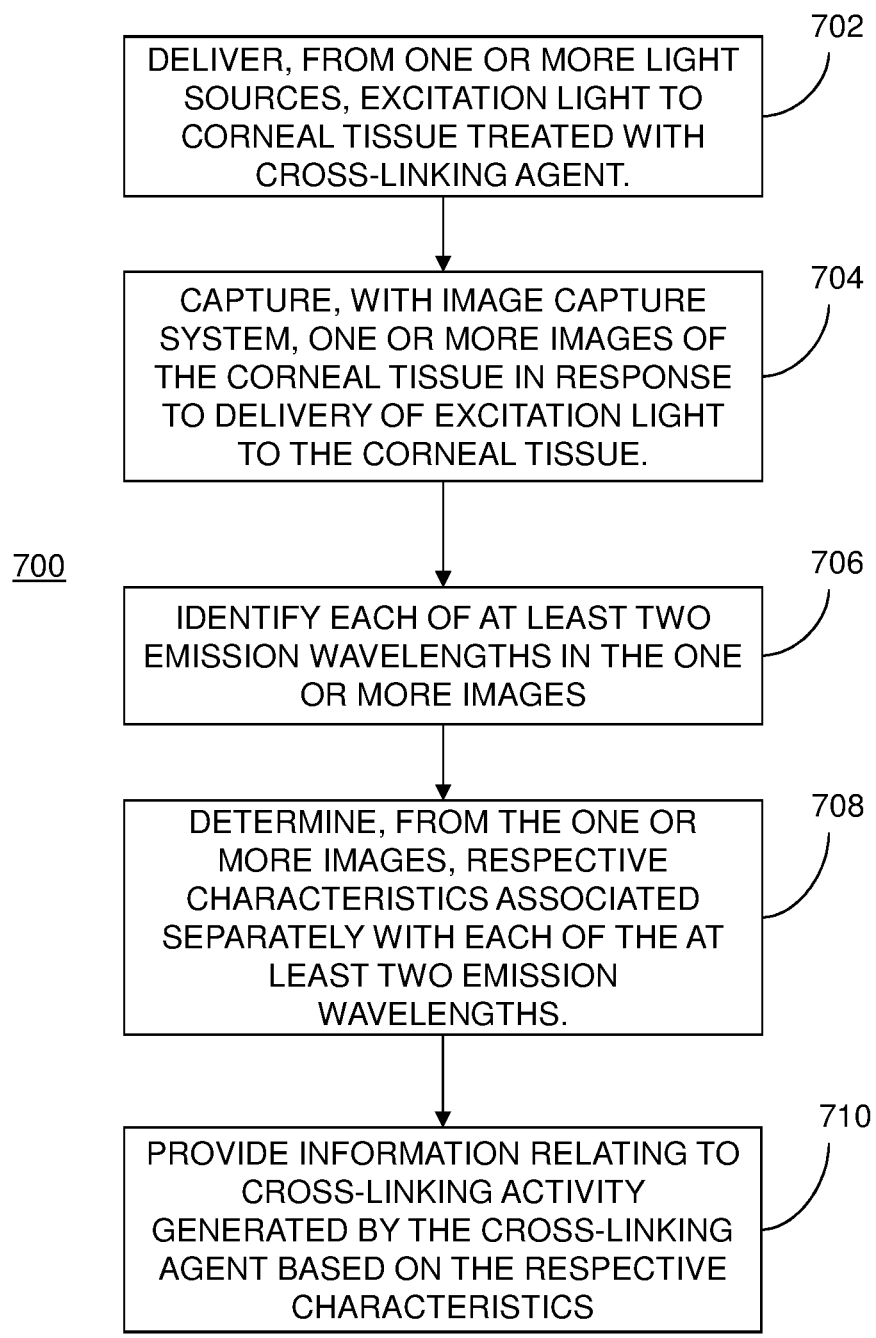
FIG. 9 illustrates an example method employing a dosimetry system, according to aspects of the present disclosure.

Referring to FIG. 8, an example treatment system 500 includes the example dosimetry system 300, which can provide feedback on the progress of cross-linking activity in the cornea 2. The example dosimetry system 300 determines the presence/distribution of the cross-linking agent 130 via fluorescence emission 502, and passes this as information 504 to the controller 520. The information 504 can indicate the progress of cross-linking activity as the presence/distribution of the cross-linking agent 130 changes with photoactivation.

As described above, the example dosimetry system 300 may indicate that the treatment system 500 has not applied and photoactivated sufficient cross-linking agent 130 to achieve the desired cross-linking activity. In response, the applicator 132 may be employed as described above to apply additional doses of the cross-linking agent 130.

The controller 520 can also use the information 504 to determine how to adjust the application of photoactivating light and to send signals 506 to a photoactivation system 510 accordingly. The photoactivation system 510, for instance, may include the light source 110 and the optical elements 112 as described above.

Furthermore, the safety of the cross-linking treatment is enhanced with feedback from the example dosimetry system 300. For instance, the controller 520 for the treatment system 500 can automatically cease further application of photoactivating light when the feedback indicates that there is no longer any cross-linking agent 130 in the corneal tissue to be photoactivated.

In some systems, the images of the fluorescence emission are taken by a monochrome imaging system and the intensity of the fluorescence is determined from the monochrome image to determine the amount of cross-linking agent in the section of corneal tissue in the image (e.g., a cross-section of the cornea situated at a particular depth). While the measurement of total intensity of the fluorescence emission from the section of corneal tissue yields useful information, separate evaluation of different wavelengths emitted by the fluorescing cross-linking agent may provide additional useful information about the progress of the cross-linking treatment.

In a simplified example, a fluorescing cross-linking agent may emit light of wavelength $\lambda_1$ at intensity $I_1$ and light of wavelength $\lambda_2$ at intensity $I_2$. (Of course, as seen in FIG. 7A, a fluorescing cross-linking agent typically emits a continuum of different wavelengths in a range rather than only two distinct wavelengths $\lambda_1$ and $\lambda_2$ as described in this example.) In some systems, a monochrome imaging system may capture light of both wavelengths $\lambda_1$ and $\lambda_2$ for a section (e.g., a pixel) of the image, and the intensity of the light determined from the section in the image is based on both $I_1$ and $I_2$. The wavelengths $\lambda_1$ and $\lambda_2$ are not readily distinguishable in the section of the image. Separately evaluating the intensity $I_1$ for wavelength $\lambda_1$ and the intensity $I_2$ for wavelength $\lambda_2$, however, may provide greater information about the underlying cross-linking activity that is occurring in the section of the image. Moreover, further information may be determined when spatially evaluating the emission of wavelengths $\lambda_1$ and $\lambda_2$ in different sections across the image.

As described above, cross-linking activity with riboflavin is generated by the photochemical kinetic reactions (r1)-(r26) involving different by-products from the photoactivation of the cross-linking agent. Over time, the different reactions may result in the emission of different wavelengths at different intensities. As such, evaluating the emission of different wavelengths can provide information on the different reactions which generate the different wavelengths. Different reactions produce different respective fluorescence emissions that can be measured by evaluating separate wavelengths in a range. A monochrome image does not allow this evaluation of separate wavelengths.

Information on the different reactions occurring at a given time may indicate the progress of the cross-linking treatment and may be employed to adjust the cross-linking treatment according to different parameters as described above. Indeed, as described above, the example dosimetry system 300 may be employed with the example system 100 of FIGS. 3 and 4. The example dosimetry 300 can provide feedback on the presence and distribution of the cross-linking agent 130 during treatment to allow the example system 100 to determine whether the desired three-dimensional distribution of cross-links is being achieved and/or whether treatment parameters can be further optimized.

To allow different wavelengths of light to be distinguishable in the captured images, the imaging system 340 shown in FIG. 6 may be configured to employ hyperspectral imaging. Hyperspectral imaging obtains spectral information for each section (e.g., pixel) in an image, where the spectral information provides distinct information for different wavelengths. For example, the hyperspectral imaging system 340 can be tuned to provide information for a range of wavelengths from approximately 365 nm to approximately 700 nm, which covers the fluorescence emission spectrum for riboflavin as shown in FIG. 7A. The range may also cover the spectrum for other effects, such as scattering, which may provide additional information. In some embodiments, the imaging system 340 may employ a hyperspectral camera based on a hyperspectral sensor monolithically integrated on a complementary metal-oxide-semiconductor (CMOS) imager. Advantageously, the hyperspectral imaging system 340 provides information for different wavelengths in a single captured image of the fluorescing cross-linking agent 130 at a given time.

Examining images of the cornea 2 from the hyperspectral imaging system 340 over time, the treatment system 300 can differentiate various spectral changes involving different wavelengths as a function of depth and correlate the various spectral changes to an amount of cross-linking activity (e.g., mol/m$^3$) in the cornea 2. In contrast to other systems that only analyze changes in total intensity for all captured wavelengths, hyperspectral imaging advantageously provides better differentiation by providing information on spectral differences and shifts as well as changes in intensity across the treated regions of corneal tissue, while maintaining spatial registration.

In the simplified example above, the hyperspectral imaging system 340 can provide information regarding each of the emitted wavelengths $\lambda_1$ and $\lambda_2$. The information indicates from what sections of the corneal tissue (e.g., associated with one or more pixel(s) in the images) each wavelength $\lambda_1$ and $\lambda_2$ is being emitted. The information also indicates the intensity of the emission of each wavelength $\lambda_1$ and $\lambda_2$. During the cross-linking treatment, shifts in spatial location and intensity for each wavelength $\lambda_1$ and $\lambda_2$ occur in response to the progress of the cross-linking activity. Correspondingly, the hyperspectral imaging system 340 allows such shifts to be monitored and evaluated to determine the progress of the cross-linking activity. The evaluation can also consider the relationship between wavelengths $\lambda_1$ and $\lambda_2$ across the treated corneal tissue.

In general, the information from the hyperspectral imaging system 340 can provide one or more images of the corneal tissue 2 when exposed to excitation light. The one or more images show at least two of the wavelengths emitted by the corneal tissue 2. Each of the at least two wavelengths can be identified from the one or more images, and respective characteristics, e.g., intensity, associated separately with each of the at least two wavelengths can be determined from the one or more images. For cross-linking treatments employing riboflavin, the respective characteristics associated with each of the at least two wavelengths can indicate cross-linking activity resulting from the photochemical kinetic reactions (r1)-(r26).

Correspondingly, FIG. 10 illustrates an example method 700 employing the example dosimetry system 300 including the hyperspectral imaging system 340. In step 702, excitation light is delivered, from one or more lights sources, to corneal tissue treated with a cross-linking agent. The excitation light causes the cross-linking agent to fluoresce by emitting an emission light at a plurality of emission wavelengths. In step 704, one or more images of the corneal tissue are captured, with the hyperspectral imaging system 340, in response to the delivery of the excitation light to the corneal tissue. The one or more images indicate at least two of the emission wavelengths of the emission light. In step 706, each of the at least two emission wavelengths in the one or more images is identified. In step 708, respective characteristics, e.g., intensity, associated separately with each of the at least two emission wavelengths are determined from the one or more images. The respective characteristics may provide information about the presence/distribution of the cross-linking agent in the corneal tissue. Accordingly, step 710 can provide information relating to cross-linking activity generated by the cross-linking agent in the corneal tissue based on the respective characteristics associated with each of the at least two emission wavelengths. This information may be electronically communicated to other systems and/or displayed or otherwise presented physically via a user interface (e.g., computer monitor, printer, etc.).

A plurality of segments of the corneal tissue can be identified in the one or more images captured by the hyperspectral imaging system 340. For instance, the plurality of segments of the corneal tissue 2 may correspond to pixels in the one or more images. Furthermore, the segments may be identified from cross-sectional images captured from varying depths in the corneal tissue 2. By capturing the one or more images over a period of time, the hyperspectral imaging system 340 can allow changes over the period of time in the respective characteristics and thus the cross-linking activity to be determined. Accordingly, the respective characteristics for the at least two emission wavelengths at a given time and from a given segment of the corneal tissue can be correlated to particular photochemical kinetic reactions to indicate temporal and spatial information on the state of the cross-linking treatment.

The use of riboflavin as the cross-linking agent and UV light as the photo-activating light in the embodiments above is described for illustrative purposes only. In general, other types of cross-linking agents may be alternatively or additionally employed according to aspects of the present disclosure. Thus, for example Rose Bengal (4,5,6,7-tetrachloro-2',4',5',7'-tetraiodofluorescein) may be employed as a cross-linking agent. Rose Bengal has been approved for application to the eye as a stain to identify damage to conjunctival and corneal cells. However, Rose Bengal can also initiate cross-linking activity within corneal collagen to stabilize the corneal tissue and improve its biomechanical strength. Like Riboflavin, photoactivating light may be applied to initiate cross-linking activity by causing the Rose Bengal to general oxygen and/or other radicals in the corneal tissue. The photoactivating light may include, for example, UV light or green light. The photoactivating light, for instance, may include photons having energy levels sufficient to individually convert $O_2$ into singlet oxygen, or may include photons having energy levels sufficient to convert $O_2$ into singlet oxygen in combination with other photons, or any combination thereof.

Although embodiments of the present disclosure may describe stabilizing corneal structure after treatments, such as LASIK surgery, it is understood that aspects of the present disclosure are applicable in any context where it is advantageous to form a stable structure of corneal tissue through cross-linking. Furthermore, while aspects of the present disclosure are described in connection with the re-shaping and/or strengthening of corneal tissue via cross-linking the corneal collagen fibrils, it is specifically noted that the present disclosure is not limited to cross-linking corneal tissue, or even cross-linking of tissue. Aspects of the present disclosure apply generally to the controlled cross-linking of fibrous matter and optionally according to feedback information. The fibrous matter can be collagen fibrils such as found in tissue or can be another organic or inorganic material that is arranged, microscopically, as a plurality of fibrils with the ability to be reshaped by generating cross-links between the fibrils. Similarly, the present disclosure is not limited to a particular type of cross-linking agent or activating element, and it is understood that suitable cross-linking agents and activating elements can be selected according to the particular fibrous material being reshaped and/or strengthened by cross-linking. Furthermore, aspects of the present disclosure can be employed to monitor any type of photoactive marker and are not limited to cross-linking agents.

As described above, according to some aspects of the present disclosure, some or all of the steps of the above-described and illustrated procedures can be automated or guided under the control of a controller (e.g., the controller 120). Generally, the controllers may be implemented as a combination of hardware and software elements. The hardware aspects may include combinations of operatively coupled hardware components including microprocessors, logical circuitry, communication/networking ports, digital filters, memory, or logical circuitry. The controller may be adapted to perform operations specified by a computer-executable code, which may be stored on a computer readable medium.

As described above, the controller may be a programmable processing device, such as an external conventional computer or an on-board field programmable gate array (FPGA) or digital signal processor (DSP), that executes software, or stored instructions. In general, physical processors and/or machines employed by embodiments of the present disclosure for any processing or evaluation may include one or more networked or non-networked general purpose computer systems, microprocessors, field programmable gate arrays (FPGA's), digital signal processors (DSP's), micro-controllers, and the like, programmed according to the teachings of the example embodiments of the present disclosure, as is appreciated by those skilled in the computer and software arts. The physical processors and/or machines may be externally networked with the image capture device(s), or may be integrated to reside within the image capture device. Appropriate software can be readily prepared by programmers of ordinary skill based on the teachings of the example embodiments, as is appreciated by those skilled in the software art. In addition, the devices and subsystems of the example embodiments can be implemented by the preparation of application-specific integrated circuits or by interconnecting an appropriate network of conventional component circuits, as is appreciated by those skilled in the electrical art(s). Thus, the example embodiments are not limited to any specific combination of hardware circuitry and/or software.

Stored on any one or on a combination of computer readable media, the example embodiments of the present disclosure may include software for controlling the devices and subsystems of the example embodiments, for driving the devices and subsystems of the example embodiments, for enabling the devices and subsystems of the example embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the example embodiments of the present disclosure can include any suitable interpretable or executable code mechanism, including but not limited to scripts, interpretable programs, dynamic link libraries (DLLs), Java classes and applets, complete executable programs, and the like. Moreover, parts of the processing of the example embodiments of the present disclosure can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the invention. It is also contemplated that additional embodiments according to aspects of the present disclosure may combine any number of features from any of the embodiments described herein.

What is claimed is:
1. A system for treatment of corneal tissue, comprising:
one or more light sources configured to generate excitation light delivered to corneal tissue treated with a cross-linking agent, the excitation light causing the cross-linking agent to fluoresce by emitting an emission light at a plurality of emission wavelengths;

an image capture system configured to capture one or more images of the corneal tissue in response to the delivery of the excitation light to the corneal tissue, the one or more images indicating at least two of the emission wavelengths of the emission light including a first emission wavelength and a second emission wavelength; and a controller configured to receive the one or more images of the corneal tissue, the controller including one or more processors and computer-readable storage media, the one or more processors configured to execute program instructions stored on the computer-readable storage media to:

identify each of the at least two emission wavelengths in the one or more images;

determine, from the one or more images, a first measurement associated with the first emission wavelength and a second measurement associated with the second emission wavelength; and provide information relating to cross-linking activity generated by the cross-linking agent in the corneal tissue based on the first measurement associated with the first emission wavelength and the second measurement associated with the second emission wavelength.

2. The system of claim 1, wherein the first measurement indicates a first intensity for the first emission wavelength and the second measurement indicates a second intensity for the second emission wavelength.

3. The system of claim 1, wherein the image capture system captures the one or more images over a period of time, and the one or more processors are configured to execute the program instructions to:

determine changes over the period of time in the first measurement and the second measurement; and provide temporal information relating to changes in the cross-linking activity over the period of time based on the changes in the first measurement and the second measurement.

4. The system of claim 1, wherein the one or more processors are configured to execute the program instructions to:

identify, in the one or more images, a plurality of segments of the corneal tissue;

identify, in each segment of the corneal tissue, each of the at least two emission wavelengths;

determine, for each segment of the corneal tissue, the first measurement and the second measurement; and provide spatial information relating to the cross-linking activity in the plurality of segments based on the first measurement and the second measurement determined for the segments of the corneal tissue.

5. The system of claim 4, wherein the plurality of segments of the corneal tissue correspond to pixels in the one or more images.

6. The system of claim 4, wherein the one or more images of the corneal tissue provide one or more cross-sectional images of the corneal tissue, the plurality of segments identified, by the one or more processors, in the one or more cross-sectional images are respectively disposed at varying depths of the cornea tissue, and the spatial information relating to the cross-linking activity is based on the first measurement and the second measurement determined for the segments of the corneal tissue respectively disposed at the varying depths of the corneal tissue.

7. The system of claim 1, wherein the image capture device includes a hyperspectral camera.

8. The system of claim 1, wherein the cross-linking agent includes riboflavin, the excitation light includes light having an excitation wavelength of approximately 365 nm and/or 450 approximately nm, and the plurality of emission wavelengths are in a range of approximately 365 nm to approximately 700 nm.

9. The system of claim 1, further comprising an applicator configured to deliver the cross-linking agent to the corneal tissue, and in response to the information relating to the cross-linking activity, the applicator is configured to deliver additional cross-linking agent to the corneal tissue.

10. The system of claim 1, wherein the one or more light sources are further configured to generate photoactivating light delivered to the corneal tissue treated with the cross-linking agent, and in response to the information relating to the cross-linking activity, the one or more light sources are configured to deliver the photoactivating light to activate the cross-linking agent.

11. The system of claim 10, wherein the cross-linking agent includes riboflavin and the photoactivating light includes ultraviolet light.

12. The system of claim 1, further comprising one or more filters configured to filter for the plurality of the emission wavelengths.

13. The system of claim 1, wherein the information relating to the cross-linking activity indicates a distribution of the cross-linking agent in the corneal tissue.

14. The system of claim 1, wherein the cross-linking agent includes riboflavin and the one or more processors are configured to execute the program instructions to determine, from the respective characteristics, the cross-linking activity resulting from reactions involving reactive oxygen species (ROS), including at least singlet oxygen, peroxides, superoxides, and hydroxyl radicals, and reactions not involving oxygen.

15. A method for treatment of corneal tissue, comprising:

delivering, from one or more light sources, excitation light to corneal tissue treated with a cross-linking agent, the excitation light causing the cross-linking agent to fluoresce by emitting an emission light at a plurality of emission wavelengths;

capturing, with an image capture system, one or more images of the corneal tissue in response to the delivery of the excitation light to the corneal tissue, the one or more images indicating at least two of the emission wavelengths of the emission light including a first emission wavelength and a second emission wavelength;

identifying each of the at least two emission wavelengths in the one or more images;

determining, from the one or more images, a first measurement associated with the first emission wavelength and a second measurement associated with the second emission wavelength; and providing information relating to cross-linking activity generated by the cross-linking agent in the corneal tissue based on the first measurement associated with the first emission wavelength and the second measurement associated with the second emission wavelength.

16. The method of claim 15, wherein the first measurement indicates a first intensity for the first emission wavelength and the second measurement indicates a second intensity for the second emission wavelength.

17. The method of claim 15, wherein capturing the one or more images includes capturing the one or more images over a period of time, determining the first measurement and the second measurement includes determining changes over the period of time in the first measurement and the second measurement, and providing information relating to the cross-linking activity includes providing temporal information relating to changes in the cross-linking activity over the period of time based on the changes in the first measurement and the second measurement.

18. The method of claim 15, further comprising identifying, in the one or more images, a plurality of segments of the corneal tissue,
- wherein identifying each of the at least two emission wavelengths includes identifying, in each segment of the corneal tissue, each of the at least two emission wavelengths,
- determining the first measurement and the second measurement includes determining the first measurement and the second measurement for each segment of the corneal tissue, and
- providing information relating to the cross-linking activity includes providing spatial information relating to the cross-linking activity in the plurality of segments based on the first measurement and the second measurement determined for the segments of the corneal tissue.

19. The method of claim 15, further comprising, in response to the information relating to the cross-linking activity, delivering, with an applicator, additional cross-linking agent to the corneal tissue.

20. The method of claim 15, further comprising, in response to the information relating to the cross-linking activity, delivering, with the one or more light sources, photoactivating light to activate the cross-linking agent.

* * * * *